United States Patent
Madabhushi et al.

(10) Patent No.: US 10,943,348 B2
(45) Date of Patent: Mar. 9, 2021

(54) PREDICTING RESPONSE TO ANTI-VASCULAR ENDOTHELIAL GROWTH FACTOR THERAPY WITH COMPUTER-EXTRACTED MORPHOLOGY AND SPATIAL ARRANGEMENT FEATURES OF LEAKAGE PATTERNS ON BASELINE FLUORESCEIN ANGIOGRAPHY IN DIABETIC MACULAR EDEMA

(71) Applicants: Case Western Reserve University, Cleveland, OH (US); The Cleveland Clinic Foundation, Cleveland, OH (US)

(72) Inventors: Anant Madabhushi, Shaker Heights, OH (US); Prateek Prasanna, Cleveland, OH (US); Justis Ehlers, Cleveland, OH (US); Sunil Srivastava, Cleveland, OH (US)

(73) Assignees: Case Western Reserve University, Cleveland, OH (US); The Cleveland Clinic Foundation, Cleveland, OH (US)

(*) Notice: Subject to any disclaimer, the term of this patent is extended or adjusted under 35 U.S.C. 154(b) by 95 days.

(21) Appl. No.: 16/415,833

(22) Filed: May 17, 2019

(65) Prior Publication Data
US 2020/0027209 A1 Jan. 23, 2020

Related U.S. Application Data

(60) Provisional application No. 62/699,918, filed on Jul. 18, 2018.

(51) Int. Cl.
*G06K 9/46* (2006.01)
*G06T 7/00* (2017.01)
(Continued)

(52) U.S. Cl.
CPC .......... *G06T 7/0012* (2013.01); *A61B 3/1241* (2013.01); *A61B 5/4848* (2013.01);
(Continued)

(58) Field of Classification Search
CPC ..... G06T 7/00; G06T 7/11; G06T 7/12; G06T 7/13; G06T 7/0012; G06T 7/0016;
(Continued)

(56) References Cited

U.S. PATENT DOCUMENTS

| | | | |
|---|---|---|---|
| 8,787,628 B1 * | 7/2014 | Derakhshani | G06K 9/00899 382/117 |
| 10,052,016 B2 * | 8/2018 | Ehlers | A61B 3/102 |
| 2017/0156582 A1 * | 6/2017 | Ehlers | G16H 50/20 |

OTHER PUBLICATIONS

Moosavi et al. ("Imaging Features of Vessels and Leakage Patterns Predict Extended Interval Aflibercept Dosing Using Ultra-Widefield Angiography in Retinal Vascular Disease: Findings from the PERMEATE Study", IEEE Transactions on Biomedical Engineering, Published on Aug. 21, 2020, pp. 1-10. (Year: 2020).*

* cited by examiner

*Primary Examiner* — Duy M Dang
(74) *Attorney, Agent, or Firm* — Eschweiler & Potashnik, LLC

(57) ABSTRACT

Embodiments facilitate prediction of anti-vascular endothelial growth (anti-VEGF) therapy response in DME patients. A first set of embodiments discussed herein relates to training of a machine learning classifier to determine a prediction for response to anti-VEGF therapy based on a set of graph-network features and a set of morphological features generated based on FA images of tissue demonstrating DME. A second set of embodiments discussed herein relates to determination of a prediction of response to anti-VEGF therapy for a DME patient (e.g., non-rebounder vs. rebounder, response vs. non-response) based on a set of
(Continued)

graph-network features and a set of morphological features generated based on FA imagery of the patient.

20 Claims, 11 Drawing Sheets

(51) Int. Cl.
*G06K 9/62* (2006.01)
*G06T 7/32* (2017.01)
*G06T 7/11* (2017.01)
*G06T 5/50* (2006.01)
*G06T 5/20* (2006.01)
*A61B 3/12* (2006.01)
*A61B 5/00* (2006.01)

(52) U.S. Cl.
CPC .......... *A61B 5/7257* (2013.01); *A61B 5/7267* (2013.01); *A61B 5/7275* (2013.01); *G06K 9/46* (2013.01); *G06K 9/628* (2013.01); *G06K 9/6262* (2013.01); *G06T 5/20* (2013.01); *G06T 5/50* (2013.01); *G06T 7/11* (2017.01); *G06T 7/32* (2017.01); *G06K 2209/05* (2013.01); *G06T 2207/10064* (2013.01); *G06T 2207/20072* (2013.01); *G06T 2207/20076* (2013.01); *G06T 2207/20081* (2013.01); *G06T 2207/20224* (2013.01); *G06T 2207/30041* (2013.01); *G06T 2207/30101* (2013.01)

(58) Field of Classification Search
CPC .. G06T 7/60; G06T 7/174; G06T 1/00; G06T 7/0085; G06T 2207/10116; G06T 2207/30004; G06T 5/40; G06T 2207/30068; G06T 7/0083; G06T 7/0081; G06T 7/32; G06T 5/50; G06T 5/20; G06T 7/136; G06T 7/162; G06T 2207/30101; G06T 2207/30041; G06T 2207/10064; G06T 2207/20072; G06T 2207/20081; G06T 2207/20084; G06T 2207/20076; G06T 2207/20224; G01N 33/4833; G01N 33/48; G01N 33/5091; G06K 9/4604; G06K 9/52; G06K 9/6267; G06K 9/66; G06K 9/46; G06K 9/62; G06K 9/628; G06K 9/6262; G06K 2209/05; G06K 9/6296; G06K 9/469; G06K 9/34; G06F 19/321; A61B 5/02007; A61B 5/7264; A61B 5/742; A61B 3/1241; A61B 5/4848; A61B 5/7267; A61B 5/7257; A61B 5/7275; A61B 3/12; A61B 3/102; A61B 5/00; A61B 5/0071; A61B 5/0261
See application file for complete search history.

| Feature set | Number of features | Feature Description |
|---|---|---|
| Leakage graphs | 51 | Voronoi Diagram: Polygon area, perimeter, chord length; Delaunay Triangulation: Triangle side length, area; Minimum Spanning Tree: Edge length statistics; Nearest Neighbors: Density of leakage spots, distance to nearest leakage |
| Leakage Morphology | 100 | Area, Mean Intensity/Intensity Range of leakage, Mean Intensity/Intensity Range Around leakage, Eccentricity Perimeter, Smoothness, Invariant Moment 1-7, Fractal Dimension, Fourier Descriptor 1-10 (Mean, Std. Dev., Median, range, skewness, kurtosis of each) |

410 — Description of quantitative imaging feature sets

Figure 4

PREDICTING RESPONSE TO ANTI-VASCULAR ENDOTHELIAL GROWTH FACTOR THERAPY WITH COMPUTER-EXTRACTED MORPHOLOGY AND SPATIAL ARRANGEMENT FEATURES OF LEAKAGE PATTERNS ON BASELINE FLUORESCEIN ANGIOGRAPHY IN DIABETIC MACULAR EDEMA

CROSS REFERENCE TO RELATED APPLICATIONS

This application claims the benefit of U.S. Provisional Patent Application No. 62/699,918 filed Jul. 18, 2018, the contents of which are herein incorporated by reference in their entirety.

FEDERAL FUNDING NOTICE

This invention was made with government support under the grant(s) CA199374, CA202752, CA208236, CA216579, CA220581, CA239055 and RR012463 awarded by the National Institutes of Health. Also grants W81XWH-18-1-0440, W81XWH-15-1-0558, and W81XWH-16-1-0329 awarded by the Department of Defense. The government has certain rights in the invention.

BACKGROUND

Diabetic macular edema (DME) is a leading cause of vision loss in diabetic patients. The underlying cause for the onset of DME is the degradation of the blood-retinal barrier. The primary function of the blood-retinal barrier is maintaining extracellular fluid at an optimal range. Vascular endothelial growth factor (VEGF) is a catalyst in altering the permeability of the blood-retinal barrier, thereby initiating a cascade of events that ultimately results in a loss of visual acuity. Fluorescein angiography (FA) and spectral-domain optical coherence tomography (SD-OCT) are the primary imaging techniques used to recognize and diagnose DME. A multimodal imaging approach that includes using FA in combination with SD-OCT provides images of vasculature and other eye structures to identify key features such as level, location, and amount of leakage.

First-line treatments for DME include using anti-VEGF agents to inhibit the effects VEGF has on increasing the permeability of the blood-retinal barrier. Because VEGF also increases the chance of leakage, it is expected that anti-VEGF treatment should decrease the amount of leakage suffered by DME patients. Anti-VEGF treatments also have a peripheral effect of modifying the disease burden and may allow for extended time in between treatments. Some existing treatment parameters used to determine efficacy of anti-VEGF treatment rely on clinicians to make a judgment call based on a minor qualitative difference of retinal scans, and thus may suffer from sub-optimal inter-reviewer, or intra-reviewer, reliability. Other existing approaches involve clinicians taking a fluid assessment, which is too invasive to demand from all DME patients. Thus, existing approaches to determining efficacy of anti-VEGF treatment are sub-optimal.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 4 illustrates a table of graph features and morphology features according to various embodiments discussed herein.

DETAILED DESCRIPTION

Figure 1:
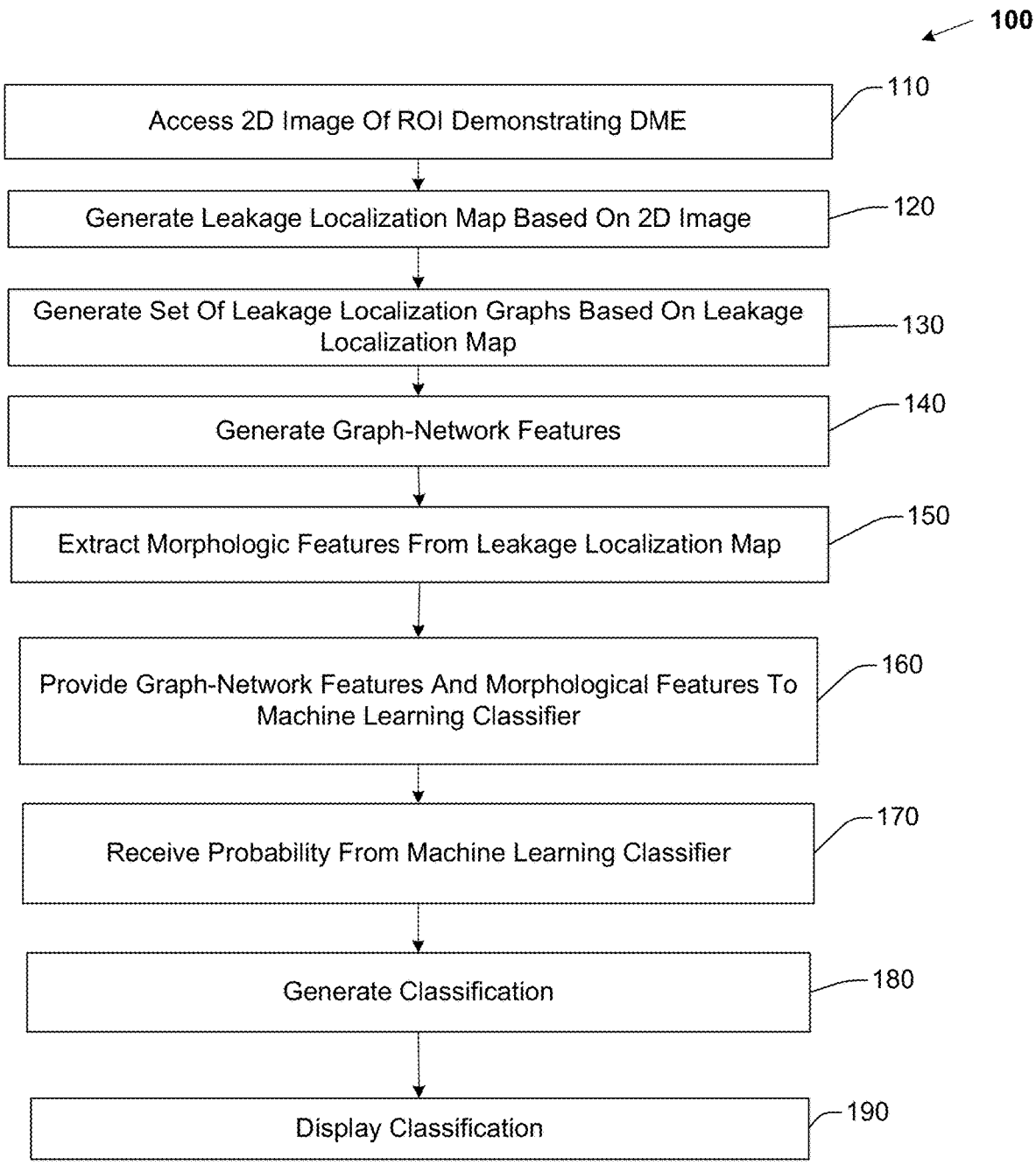
FIG. 1 illustrates a workflow diagram of an example method or set of operations that employs a machine learning classifier to distinguish non-rebounders from rebounders according to various embodiments discussed herein.

Diabetic macular edema (DME) is one of the leading causes of vision loss in patients with diabetic mellitus. DME is clinically defined as a retinal thickening of the center of the macula or thickening within 500µ of the macula's center. While DME's origin is multifactorial, a major catalyst in the eventual loss in visual acuity (VA) stems from the disruption of the blood-retinal barrier, leading to fluid accumulation within intra-retinal layers of the macula. When evaluating DME, fluorescein angiography (FA) imagery provides information on vascular leakage and non-perfusion. The use of ultra-wide field FA (UWFA) imagery provides near-panretinal assessment of disease burden.

A rise in vascular endothelial growth factor (VEGF) is linked to an increase in permeability in the blood-retinal barrier, thereby initiating a cascade of events which ultimately leads to a loss in VA. Anti-VEGF therapy has emerged as a first-line treatment to DME. Anti-VEGF therapy may improve clinical outcomes by improving VA and reducing macular edema. However, there is a lack of knowledge surrounding the impact of anti-VEGF treatment on the underlying pathophysiology of retinal vasculature characteristics, including blood-vessel arrangement, vascular leakage, and ischemia. Additionally, discriminating imaging features that may be important biomarkers for treatment response have not been identified in existing approaches. While existing clinical parameters such as macula thickness are now standardized in treatment care, there is still a void in how much information they possess and to what level of accuracy they have when used as a prognostic tool. Thus there is a need for validated, image-derived biomarkers that can be used as non-invasive, prognostic features to facilitate determining how certain patients respond to anti-VEGF treatment, and further to facilitate selection of patients that would most benefit from anti-VEGF treatment.

Due to the important role that leakage plays in DME, existing methods that focus on imaging DME include the use of FA. FA involves administering sodium fluorescein intravenously to evaluate the circulatory ability of retinal blood vessels. Under normal conditions, the injected fluorescein cannot pass through tight junctions of capillaries. However, in the case of DME, the blood vessels are damaged, resulting in leakage of fluorescein. FA also facilitates the recognition of microaneurysms, ischemia, and abnormal vessels. Indicators for these symptoms manifest in the form of hyper fluorescence.

Some existing approaches to predicting anti-VEGF therapy response include studying leakage patterns to learn more about the pathophysiology behind DME, however, these approaches are limited to identifying different types of DME based on leakage appearance (diffuse DME vs. focal DME). To distinguish either subcategory from each other (e.g., diffuse DME vs. focal DME) it is essential to examine an FA image displaying leakage patterns. Diffuse DME presents in the form of generalized areas of leakage in the area centralis, while focal DME presents as discrete areas of leakage due to the effect of microaneurysms. Analysis of leakage on SD-OCT imagery includes using the location of leakage to quantify changes in optical reflectivity, which is a key statistic for clinical follow-ups.

Embodiments extract quantitative features from leakage images and predict patient outcomes based on the extracted features. Embodiments extract features from baseline (e.g., pre-anti-VEGF treatment) FA images that quantify the leakage shape, size, density, and inter-object (e.g., inter-leakage patch) distance attributes. Embodiments identify features that are different between the two phenotypes (e.g., non-rebounder, rebounder), and train a machine learning classifier with the identified features to predict response to anti-VEGF treatment. Embodiments may access an FA image associated with a patient demonstrating DME, extract distinguishing features from the FA image, provide the features to a machine learning classifier trained to differentiate non-rebounders from rebounders according to embodiments described herein, and generate a classification of the patient as a non-rebounder or rebounder. Embodiments extract features from FA imagery that quantify leakage shape, size, density, and inter-object distance attributes, and generate a prognostic prediction of outcome for the patient of whom the imagery is associated, based on the features, that is significantly improved compared to existing approaches that may only employ clinical parameters. Embodiments further facilitate identifying DME patients who would receive added benefit from a first course of therapy or a second, different course of therapy, and further facilitate improved treatment management in DME, compared to existing approaches that may only employ clinical parameters.

Embodiments described herein can employ techniques discussed herein for distinguishing non-rebounders from rebounders in DME via a machine learning classifier trained on FA imagery, including UWFA imagery, and features extracted from said imagery that have been identified as distinguishing between eyes associated with different phenotypes (e.g., non-rebounder, rebounder). In various embodiments, features generated or employed by various embodiments may include features that quantify leakage shape, size, density, and inter-object (e.g., leakage patch) distance attributes, including graph-based features.

Embodiments, may, for example, extract morphological and graph-based attributes or features from FA imagery to model the global properties and spatial distribution of leakage areas on baseline FA scans of patients subsequently treated with intravitreal anti-VEGF therapy (i.e. Aflibercept) . Embodiments may provide the extracted features to a machine learning a classifier configured to distinguish between eyes tolerating extended dosing intervals and those eyes requiring more frequent dosing, based on initial response following treatment interval extension. Embodiments achieve a cross-validated area under the receiver operating characteristic curve (AUC) of at least 0.74+−0.11% using the computed imaging attributes. Edge length disorder of minimum spanning tree as determined according to various embodiments described herein shows a statistically significant difference ($p=0.007$) between the two groups (e.g., between non-rebounders vs. rebounders). In contrast, clinical parameters such as central subfield thickness and macular volume were not statistically significantly different between the two phenotypes. Embodiments thus quantify and use differences in spatial distribution of leakage areas between eyes extracted from FA imagery to facilitate improved discrimination between eyes that will exhibit favorable response to extended interval Aflibercept dosing and eyes that require more frequent dosing.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Various embodiments can employ techniques discussed herein to facilitate distinguishing non-rebounders from rebounders among DME patients. FIG. 1 illustrates a flow diagram of an example method or set of operations 100 that employs a machine learning classifier to distinguish non-rebounders from rebounders among DME patients, according to various embodiments discussed herein. A non-rebounder is an eye that will exhibit favorable response to extended interval anti-VEGF (e.g., Aflibercept) dosing, compared to eyes that require more frequent dosing (rebounders). In one embodiment, a non-rebounder is defined as a favorable responder to anti-VEGF therapy after at least three cycles of anti-VEGF administration. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The method or set of operations 100 includes, at 110, accessing a digitized image associated with a patient. The digitized image includes a region of interest (ROI) demonstrating diabetic macular edema (DME) pathology. The digitized image has a plurality of pixels, a pixel having an intensity. In one embodiment, the digitized image is a fluorescein angiography (FA) image. The accessed digitized image (e.g., FA image) can be stored in memory locally or remotely, and can be obtained via a medical imaging device one of concurrently with method or operations 100 (e.g., via a medical imaging device implementing method or operations 100) or prior to method or operations 100. In one embodiment, the digitized image is a two-dimensional (2D) fluorescein angiography (FA) image or ultra-wide field FA (UWFA) image of a region of interest (ROI) demonstrating diabetic macular edema (DME), where the image is associated with a patient, where the image has a plurality of pixels, a pixel having an intensity. Accessing the digitized image (e.g., FA image) includes acquiring electronic data, reading from a computer file, receiving a computer file, reading from a computer memory, or other computerized activity not practically performed in the human mind.

Operations 100 also includes, at 120, generating a leakage localization mask based on the FA image. The leakage localization mask includes a plurality of leakage patches. In one embodiment, generating the leakage localization mask also includes optionally generating a panretinal vascular skeletonized map, or a microaneurysm mask. One suitable approach for generating a leakage localization mask is described in Ehlers, J. P., Wang, K., Vasanji, A., Hu, M., and Srivastava, S. K., "Automated quantitative characterization of retinal vascular leakage and microaneurysms in ultra-widefield fluorescein angiography," British Journal of Ophthalmology 101(6), 696{699 (2017). Other techniques for generating a leakage localization mask may be employed. Generating the leakage localization mask includes acquiring electronic data, reading from a computer file, receiving a computer file, reading from a computer memory, or other computerized activity not practically performed in the human mind.

Figure 3:
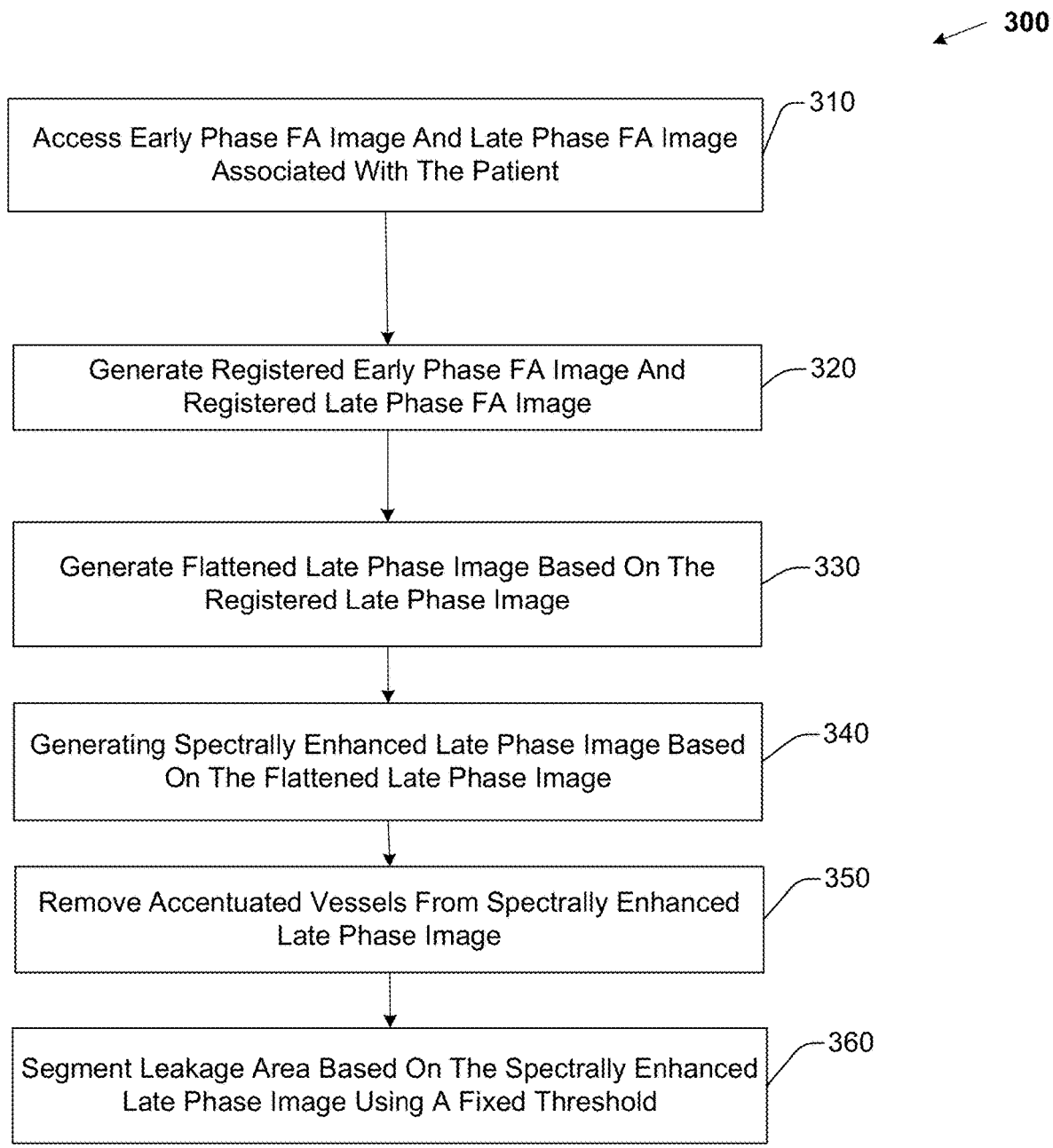
FIG. 3 illustrates a workflow diagram of an example method or set of operations for generating a leakage localization mask on FA imagery according to various embodiments discussed herein.

FIG. 3 illustrates one exemplary methodology or set of operations 300 suitable for generating the leakage localization mask. In this embodiment, generating the leakage localization mask includes, at 310, accessing an early phase FA image and a late phase FA image associated with the patient. Generating the leakage localization mask also includes, at 320, generating a registered early phase FA image and a registered late phase FA image by registering the early phase FA image with the late phase FA image. In one embodiment, the early phase FA image is registered with the late phase FA image using Fourier correlation of retinal vascular patterns. Generating the leakage localization mask also includes, at 330, generating a flattened late phase image based on the registered late phase image. In one embodiment, generating the flattened late phase image includes removing an intensity gradient of the optic disc to an image periphery. Generating the leakage localization mask also includes, at 340, generating a spectrally enhanced late phase image based on the flattened late phase image. In one embodiment, generating the spectrally enhanced late phase image includes equalizing intensity of leakage regions represented in the flattened late phase image. Equalizing the intensity of leakage regions may include histogram equalization. The spectrally enhanced late phase image may include accentuated vessels. Generating the leakage localization mask also includes, at 350 removing accentuated vessels from the spectrally enhanced late phase image. In one embodiment, removing accentuated vessels includes filtering vessels in the registered early phase FA image using a Gaussian convolution kernel, spectrally enhancing the filtered vessels, and subtracting the spectrally enhanced filtered vessels from the registered early phase FA image. Generating the leakage localization mask further includes, at 360, segmenting a leakage area based on the spectrally enhanced late phase image using a fixed threshold. In another embodiment, other techniques may be employed to generate the leakage localization mask.

Returning to FIG. 1, operations 100 also includes, at 130, generating a set of leakage graphs based on the leakage localization mask. A node of a member of the set of leakage graphs is a member of the plurality of leakage patches. The set of leakage graphs includes at least one leakage graph. In one embodiment, the set of leakage graphs includes a minimum spanning tree (MST) graph. In this embodiment, a node of the MST graph is a member of the plurality of leakage patches. In another embodiment, other leakage graphs may be generated. For example, Voronoi or Delaunay graphs may be generated. Generating the set of leakage graphs includes acquiring electronic data, reading from a computer file, receiving a computer file, reading from a computer memory, or other computerized activity not practically performed in the human mind.

Operations 100 also includes, at 140, generating a set of graph-network features based on the set of leakage graphs. In one embodiment, the set of graph-network features includes at least an edge length disorder of MST feature. In another embodiment, in which Voronoi or Delaunay graphs are generated, features quantifying the Voronoi or Delaunay graphs, respectively, may be computed, and the set of graph network features may include features quantifying the Voronoi or Delaunay graphs. FIG. 4 illustrates a table 410 which illustrates features which may be included in the set of graph-network features. For example, the set of graph-network features may include, for a Voronoi diagram (e.g., graph), a polygon area feature, a perimeter feature, or a chord length feature. The set of graph-network features may include, for a Delaunay triangulation (e.g., graph), a triangle side length feature, or an area feature. The set of graph-network features may include, for a minimum spanning tree graph, edge length statistics. The set of graph-network features may further include, for nearest neighbors, a density of leakage spots feature, or a distance to nearest leakage feature. In other embodiments, the set of graph-network features may include other, different graph-network features. Generating the set of graph-network features includes acquiring electronic data, reading from a computer file, receiving a computer file, reading from a computer memory, or other computerized activity not practically performed in the human mind.

Operations 100 also includes, at 150, extracting a set of morphological features based on the leakage localization mask. In one embodiment, the set of morphological features includes at least one of an area feature, a distance to N nearest neighbors feature, or a disorder of variance of distance to N nearest neighbors feature. In another embodiment, the set of morphological features may include other, different morphological features. FIG. 4 also illustrates, at 410, leakage morphology features which may be included in the set of morphological features. Extracting the set of morphological features includes acquiring electronic data, reading from a computer file, receiving a computer file, reading from a computer memory, or other computerized activity not practically performed in the human mind.

Operations 100 also includes, at 160, providing the set of graph-network features and the set of morphological features to a machine learning classifier configured to distinguish non-rebounders from rebounders in DME based on the set of graph-network features and the set of morphological features. In one embodiment, the machine learning classifier is a quadratic discriminant analysis (QDA) classifier. In another embodiment, the machine learning classifier may be another, different type of machine learning classifier, for example, a linear discriminant analysis (LDA) classifier, a support vector machine (SVM) classifier, a random forests (RF) classifier, or a deep learning classifier, including a convolutional neural network (CNN). Providing the set of graph-network features and the set of morphological features to the machine learning classifier includes acquiring electronic data, reading from a computer file, receiving a computer file, reading from a computer memory, or other computerized activity not practically performed in the human mind.

Operations 100 also includes, at 170, receiving, from the machine learning classifier, a probability that the patient is a non-rebounder. The machine learning classifier computes the probability based on the set of graph-network features and the set of morphological features. Receiving the probability includes acquiring electronic data, reading from a computer file, receiving a computer file, reading from a computer memory, or other computerized activity not practically performed in the human mind.

Operations 100 also includes, at 180, generating a classification of the patient as a non-rebounder or rebounder based, at least in part, on the probability. In various embodiments, the classification may include one or more of a most likely outcome (e.g., as determined based on the probability based on the set of graph-network features and the set of morphological features, etc.) such as non-rebounder; a probability or confidence associated with a most likely outcome; and/or associated probabilities/confidences associated with each of a plurality of outcomes (e.g., non-rebounder, rebounder). For example, in one embodiment, generating the classification includes classifying the patient associated with the ROI as a non-rebounder when the probability is >=0.5, or classifying the patient as a rebounder when the probability is <0.5. In another embodiment, other classification schemes may be employed. For example, in one embodiment, the patient may be classified as a responder or non-responder based on the probability. In one embodiment, the classification is generated with an AUC of at least 0.74+−0.11%, with a KM curve analysis in which p=0.007. Generating the classification includes acquiring electronic data, reading from a computer file, receiving a computer file, reading from a computer memory, or other computerized activity not practically performed in the human mind. Generating the classification includes acquiring electronic data, reading from a computer file, receiving a computer file, reading from a computer memory, or other computerized activity not practically performed in the human mind.

Operations 100 further includes, at 190, displaying the classification. In one embodiment, the set of operations 100 includes, at 190, displaying the classification and optionally displaying one or more of the image, the set of graph-network features, the set of morphological features, or the probability. Displaying the classification and optionally displaying one or more of the image, the set of graph-network features, the set of morphological features, or the probability may include displaying the classification and optionally displaying one or more of the image, the set of graph-network features, the set of morphological features, or the probability on a computer monitor, a smartphone display, a tablet display, or other displays. Displaying the classification and optionally displaying one or more of the image, the set of graph-network features, the set of morphological features, or the probability can also include printing the classification and optionally printing one or more of the image, the set of graph-network features, the set of morphological features, or the probability. Displaying the classification and optionally displaying one or more of the image, the set of graph-network features, the set of morphological features, or the probability can also include controlling a DME treatment response prediction system, a personalized medicine system, an FA or UWFA system, a monitor, or other display, to display operating parameters or characteristics of a machine learning classifier, during at least one of training and testing of the machine learning classifier, or during clinical operation of the machine learning classifier. By displaying the classification and optionally displaying one or more of the image, the set of graph-network features, the set of morphological features, or the probability, example embodiments provide a timely and intuitive way for a human medical practitioner to more accurately predict treatment response, to more accurately classify an ROI or a patient associated with the ROI into a treatment response category (e.g., non-rebounder, rebounder), thus improving on existing approaches to predicting DME treatment response. By displaying the classification and optionally displaying one or more of the image, the set of graph-network features, the set of morphological features, or the probability, example embodiments may further provide a timely and intuitive way for a human medical practitioner to more accurately identify DME patients as non-rebounders or rebounders, and to improve treatment management accordingly. Embodiments may further display operating parameters of the machine learning classifier.

Figure 2:
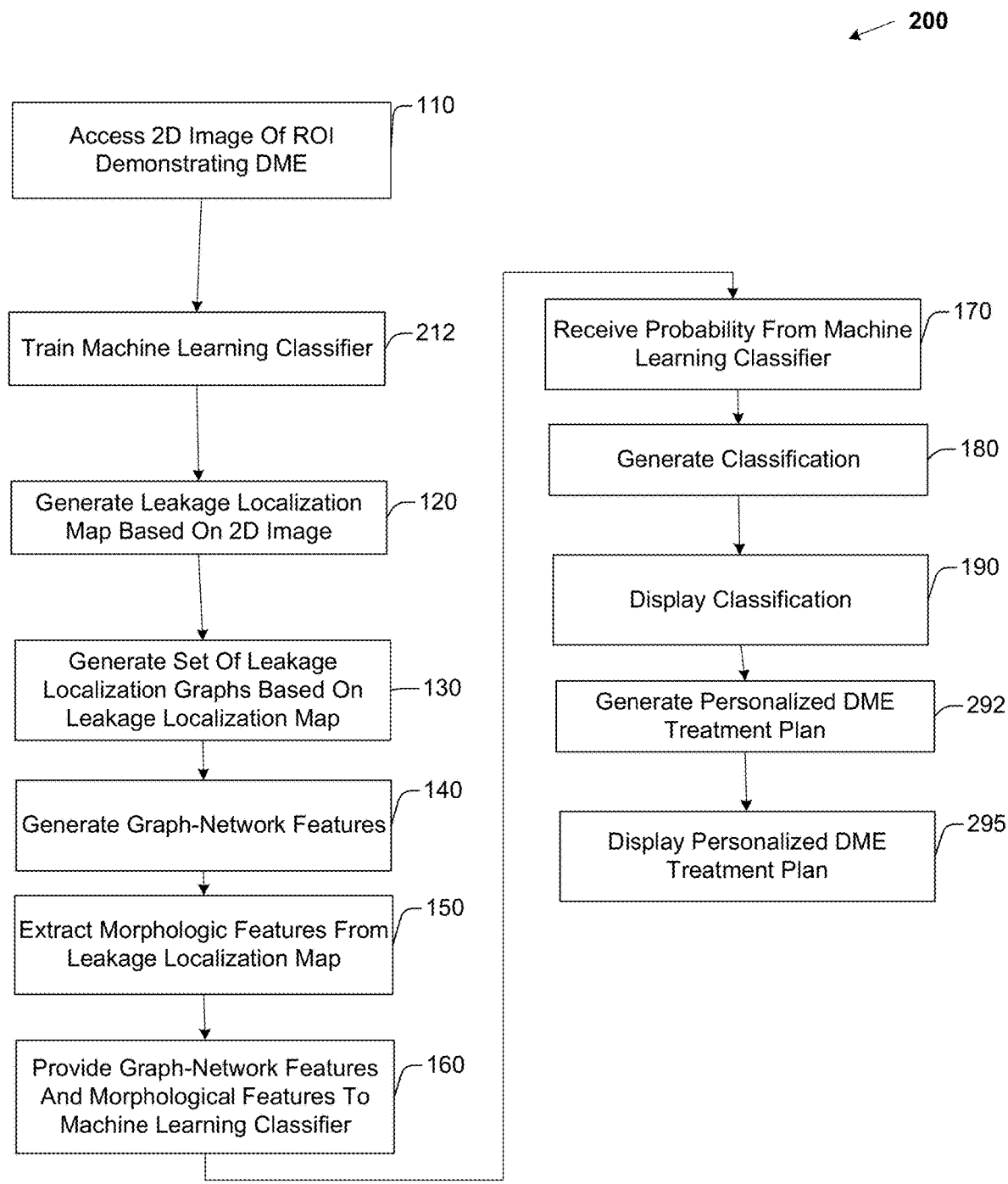
FIG. 2 illustrates a workflow diagram of an example method or set of operations that employs a machine learning classifier to distinguish non-rebounders from rebounders according to various embodiments discussed herein.

FIG. 2 illustrates a set of operations 200 that is similar to operations 100 and includes operations 110-190 as described herein, but that includes additional operations. Operations 200 includes, at 212, training the machine learning classifier.

Figure 10:
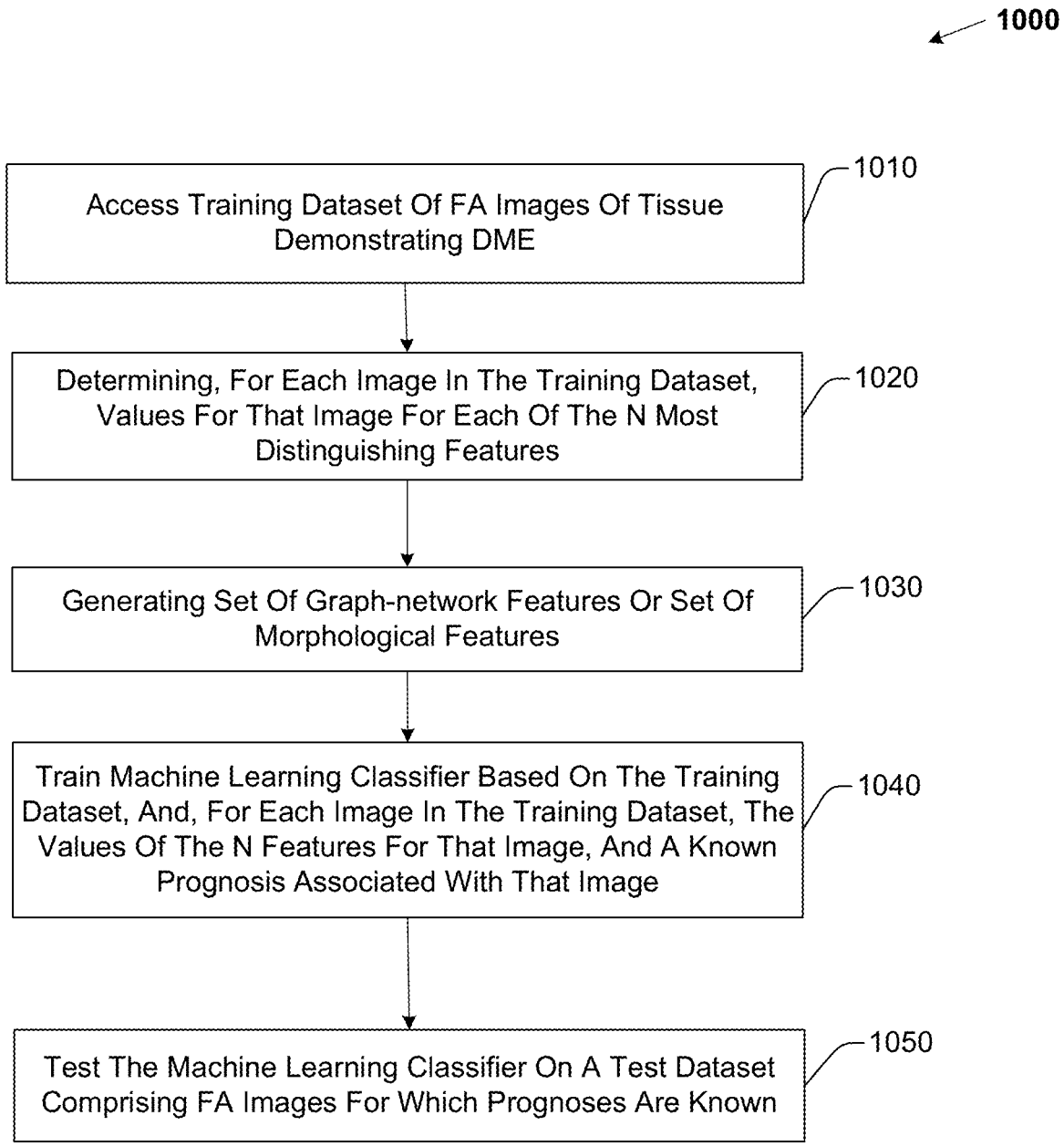
FIG. 10 illustrates a flow diagram of an example method or set of operations for training a machine learning classifier according to various embodiments discussed herein.

FIG. 10 illustrates a diagram showing an example flow of a method or set of operations 1000 that facilitates training a machine learning classifier to generate a probability that a patient associated with an ROI demonstrating DME is a non-rebounder or rebounder, based on the set of graph-network features and the set of morphological features acquired from FA (e.g., UWFA) image(s), according to various embodiments discussed herein. Method or set of operations 1000 may be employed by various embodiments described herein, including, for example, operations 200, at 212, or by apparatus 800.

Operations 1000 may include, at 1010, accessing a training dataset of FA images of tissue demonstrating DME. As explained in greater detail herein, the training dataset can comprise a plurality of FA images of tissue demonstrating DME comprising a positive set that is associated with a first classification (e.g., non-rebounder, responder) and a negative set that is associated with a different second classification (e.g., rebounder, non-responder).

Operations 1000 may also include, at 1020, determining, for each image in the training dataset, values for that image for each of the N (where N is a positive integer) most distinguishing features, including features used in generating the set of graph-network features or the set of morphological features for distinguishing non-rebounders from rebounders. The N most distinguishing features can be determined via any of a variety of algorithm or measures (e.g., sequential forward feature selection, RF, t-test, Wilcoxon rank sum, mRMR, etc.). For example, embodiments may, (e.g., to avoid the curse of dimensionality), use mRMR feature selection to select the top 3 features in a 3-fold cross-validated fashion. The features may be assigned scores based on their frequency of occurrence. The top 3 features in each fold and each run may then be used in conjunction with a machine learning classifier (e.g., QDA classifier) to distinguish non-rebounders from rebounders. The N most distinguishing features may be employed, at 1030, in generating the set of graph-network features or the set of morphological features according to various embodiments discussed herein. In other embodiments, other values for N (e.g., 5, 7) may be employed.

The set of operations 1000 can further include, at 1040, training a machine learning classifier (e.g., QDA (Quadratic Discriminant Analysis) classifier), SVM (Support Vector Machine), LDA (Linear Discriminant Analysis) classifier, DLDA (Diagonal Line Discriminant Analysis) classifier, RF (Random Forest) classifier, CNN (Convolutional Neural Network) classifier, etc.) based on the training dataset, and, for each image in the training dataset, the values of the N features for that image (e.g., the set of graph-network features, the set of morphological features), and a known prognosis (e.g., non-rebounder, rebounder) associated with that image. Based on the training dataset, and, for each image in the training dataset, the values of the N features for that image, and a known prognosis (e.g., non-rebounder, rebounder) associated with that image, the classifier can determine classes for non-rebounder and rebounder, and probability of non-rebounder or rebounder for associated feature vectors (e.g., the set of graph-network features, the set of morphological features).

The set of operations 1000 can optionally include, at 1050, testing the machine learning classifier on a test dataset comprising FA images for which prognoses are known (e.g., in a manner similar to set of operations 100, additionally comprising comparing a generated prognosis with the known prognosis). In this manner, the ability of the machine learning classifier to correctly classify patients associated with FA images as non-rebounders or rebounders based on the set of graph-network features and the set of morphological features can be estimated. In one embodiment, an independent dataset is also accessed, the independent dataset including a plurality of FA images of tissue demonstrating DME, and clinical information (e.g., tolerance of anti-VEGF therapy, central sub-field thickness, macular volume, letter scores) associated with the patients of which the plurality of FA images comprising the independent dataset is acquired. Testing the machine learning classifier may, in this embodiment, further comprise testing the machine learning classifier on an independent dataset according to various embodiments discussed herein.

Training the machine learning classifier can also include determining which graph-network features or morphological features are most discriminative in distinguishing non-rebounders from rebounders, and/or determining the optimal combination of parameters used in the computation of the probability (e.g., which features to include in the set of graph-network features or the set of morphological features, how many features to employ) can best separate a positive class from a negative class (e.g., non-rebounder from rebounder). Embodiments may generate a receiver operating characteristic curve (ROC) and calculate an associated area under the ROC (AUC).

Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. In one embodiment, the machine learning classifier is trained until at least an AUC=0.74 in distinguishing non-rebounders from rebounders is achieved.

Returning to FIG. 2, the set of operations 200 may further include, at 292, generating a personalized DME treatment plan. The personalized DME treatment plan may be generated based, at least in part, on the classification and optionally on one or more of the set of graph-network features, the set of morphological features, the probability, or the FA image. The personalized DME treatment plan may be generated for the patient of whom the image was acquired based, at least in part, on the classification and optionally on one or more of the set of graph-network features, the set of morphological features, the probability, or the FA image. Defining a personalized DME treatment plan facilitates delivering a particular treatment that will be therapeutically active to the patient, while minimizing negative or adverse effects experienced by the patient. For example, the personalized DME treatment plan may suggest a surgical treatment, may define a pharmaceutical agent dosage or schedule and/or other recommendations for DME management, for a patient, wherein the specific recommendation can depend on a classification (e.g., non-rebounder, rebounder) associated with the patient. Generating the personalized DME treatment plan includes acquiring electronic data, reading from a computer file, receiving a computer file, reading from a computer memory, or other computerized activity not practically performed in the human mind.

The set of operations 200 can further include, at 295, optionally displaying the personalized DME treatment plan according to embodiments described herein.

Techniques and aspects of various embodiments are further explained below, in connection with an example embodiment that facilitates distinguishing non-rebounders from rebounders for a patient demonstrating DME represented in FA imagery, including UWFA imagery.

Example Use Case: Spatial Arrangement of Leakage Patterns in Diabetic Macular Edema is Associated with Tolerance of Aflibercept Treatment Interval Length.

An example embodiment included training a machine learning classifier to distinguish non-rebounder DME patients from rebounder DME patients, based on example imagery of DME non-rebounders and rebounders represented in FA imagery. In this example, N=27 cases of DME were obtained from the PERMEATE clinical trial. PERMEATE is a prospective study, at the Cleveland Clinic Foundation (CCF), for treatment-nave eyes with foveal-involving edema secondary to DME or Retinal Vein Occlusion (RVO), utilizing monthly Aflibercept injection (2 mg) for the initial 6 months. Eligibility criteria included men and women >=18 years of age, foveal-involving retinal edema secondary to DME or RVO, and standardized best-corrected visual acuity of 20/25 or worse. Participants who were exposed to any prior therapy to treat DME or RVO, such as laser or pharmacotherapy were excluded from this study. Participants were also excluded if significant vitreous hemorrhage was present which limited the ability to undergo FA and collect images of the macular or retinal periphery. All the images were collected over a span of 12 months with UWFA and OCT-A taken quarterly. Additional higher-order quantitative measurements included macular ellipsoid zone (EZ)-RPE volume, en face percentage of EZ attenuation, and volumetric analysis of retinal fluid. The intravitreal aflibercept (IAI) 2 mg was utilized monthly for the first 6 months, and then administered at month 8, 10, 11, and 12. Based on the recurrence of macular edema/visual acuity worsening at visit 8 (i.e., first visit with q8 week dosing), the patients were classified into non-rebounders (N=15) and rebounders (N=12). Leakage maps were also obtained along with the FA scans.

Embodiments segment leakage represented in FA imagery. In this example, the FA scans were evaluated utilizing an automated vessel, leakage, and microaneurysm segmentation platform. This technique generated multiple masks for additional analysis including a panretinal vascular skeletonized map, a leakage localization mask, and a microaneurysm mask for each image, respectively. In this example, a leakage algorithm initially registers the early and late phase FA images for a given subject using Fourier correlation of retinal vascular patterns. This spatial registration accounts for rotation and translation of images during acquisition. Following registration, the late phase image is flattened to remove the intensity gradient from the optic disc to the image periphery. Subsequently, the late phase image is spectrally enhanced to equalize the appearance of leakage regions and enable application of a fixed threshold for segmentation of candidate leakage areas. To remove vessels that are accentuated in the late phase image by this process, vessels in the corresponding registered early phase image are filtered using a Gaussian convolution kernel, spectrally enhanced and subtracted from the late phase image.

Embodiments generate graphs to describe leakage patterns. Voronoi, Delaunay, and Minimum Spanning Tree-based graph tessellations may be used to describe the architecture of objects. Voronoi, Delaunay, and Minimum Spanning Tree-based graph tessellations are fully connected graph constructs where the centroids of objects are used as nodes and vectors connecting them are edges. Here "objects" refers to leakage patches. The statistics of different global graph measurements, e.g., size of Voronoi polygon, are extracted from the resulting graphs as quantitative features to describe the leakage spots. These features capture the architecture of the leakage spots, thus providing global information on how the leakage spots are arranged. For example, an average of Voronoi area may capture the overall density of the leakage spots, while variance of connecting edges may capture the disorder pattern of the leakage spots.

Embodiments compute morphological features based on the FA imagery. In this example, morphological features quantify the shape, size, density and inter-object distance attributes. In this example, the morphological features include area, number of objects/area, distance to N nearest neighbors, disorder of distance to N neighbors etc. FIG. 4 illustrates table 410, which illustrates different morphological and graph-based features used in this example.

Embodiments compute a statistical analysis of features extracted from FA imagery. In this example, a 151 by 1 feature vector, summarizing different attributes of leakage patches, is computed for each FA image. To avoid the curse of dimensionality, this example uses minimum redundancy maximum relevance (mRMR) feature selection to select the top 3 features in a 3-fold cross-validated fashion. The features are assigned scores based on their frequency of occurrence. The top 3 features in each fold and each run are used in conjunction with a quadratic discriminant analysis (QDA) machine learning classifier to distinguish non-rebounders from rebounders. Clinical parameters such as central subfield retinal thickness, macular volume and letter scores were evaluated at baseline visit. The statistical significance of each of these features is computed for the two groups using a Wilcoxon ranksum test. Further, the significance values are compared against the one obtained using the top discriminating image-derived feature.

Figure 5:
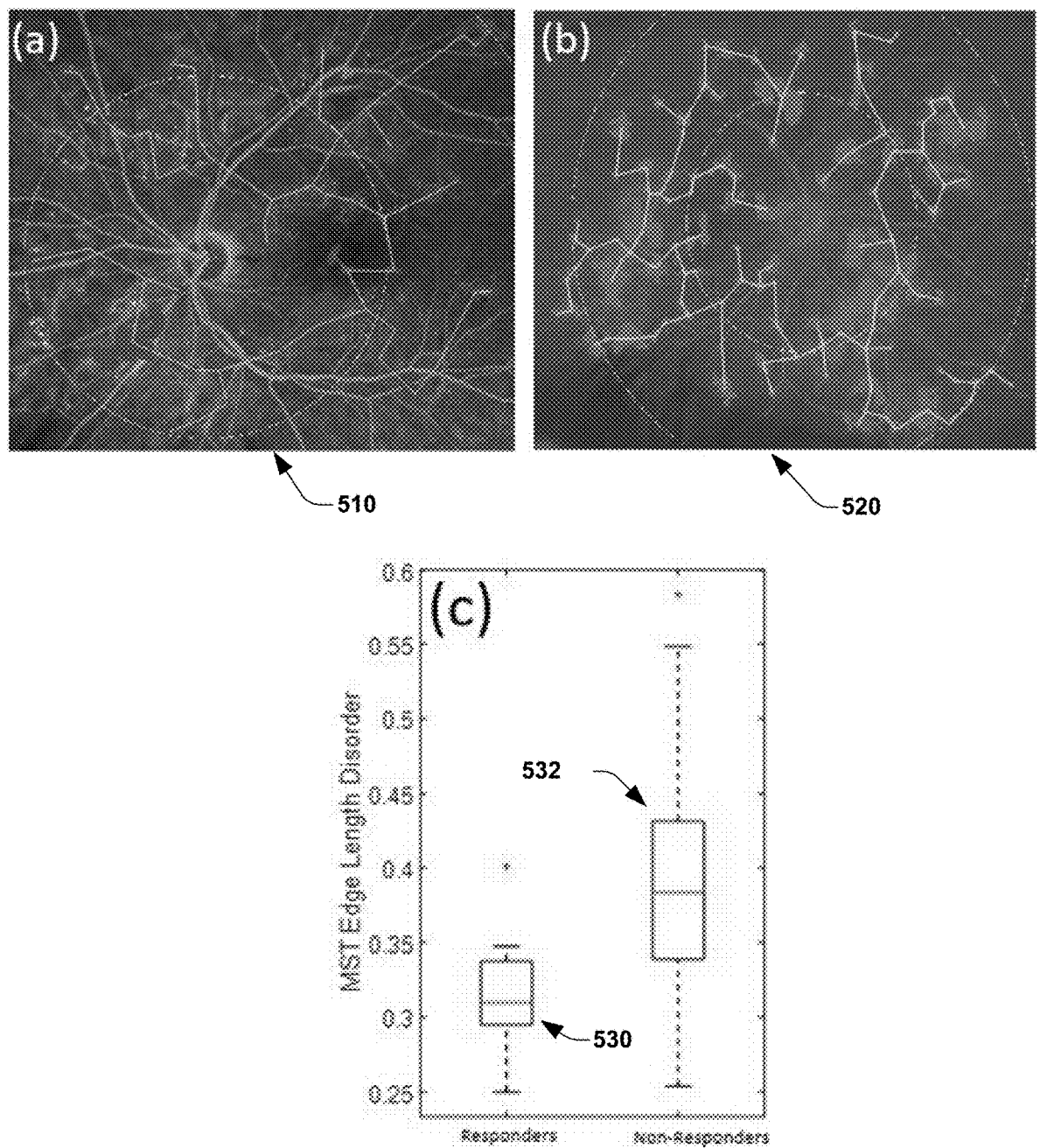
FIG. 5 illustrates example baseline FA imagery.

Embodiments described herein facilitate distinguishing eyes based on durability of treatment response using morphological and graph-based features. In this example, analysis on the training dataset the cross-validated area under the receiver operating characteristic curve was found to be 0.74+−0.11% using the computer-extracted descriptors, with the disorder of minimum spanning tree edge length showing statistical significant difference (p=0.007) between the two groups of patients. FIG. 5 illustrates at 510 and 520 example baseline FA images of a responder and a non-responder, respectively. Their corresponding leakage patches are highlighted in red, and the minimum spanning tree edges in blue. Centroids of leakage patches are used as nodes and vectors connecting them are edges. Weights are the length of the edges. Box and whisker plot 530 corresponds to the MST edge length disorder values from the non-rebounders, while box and whisker plot 532 corresponds to the MST edge length disorder from the rebounders.

Figure 6:
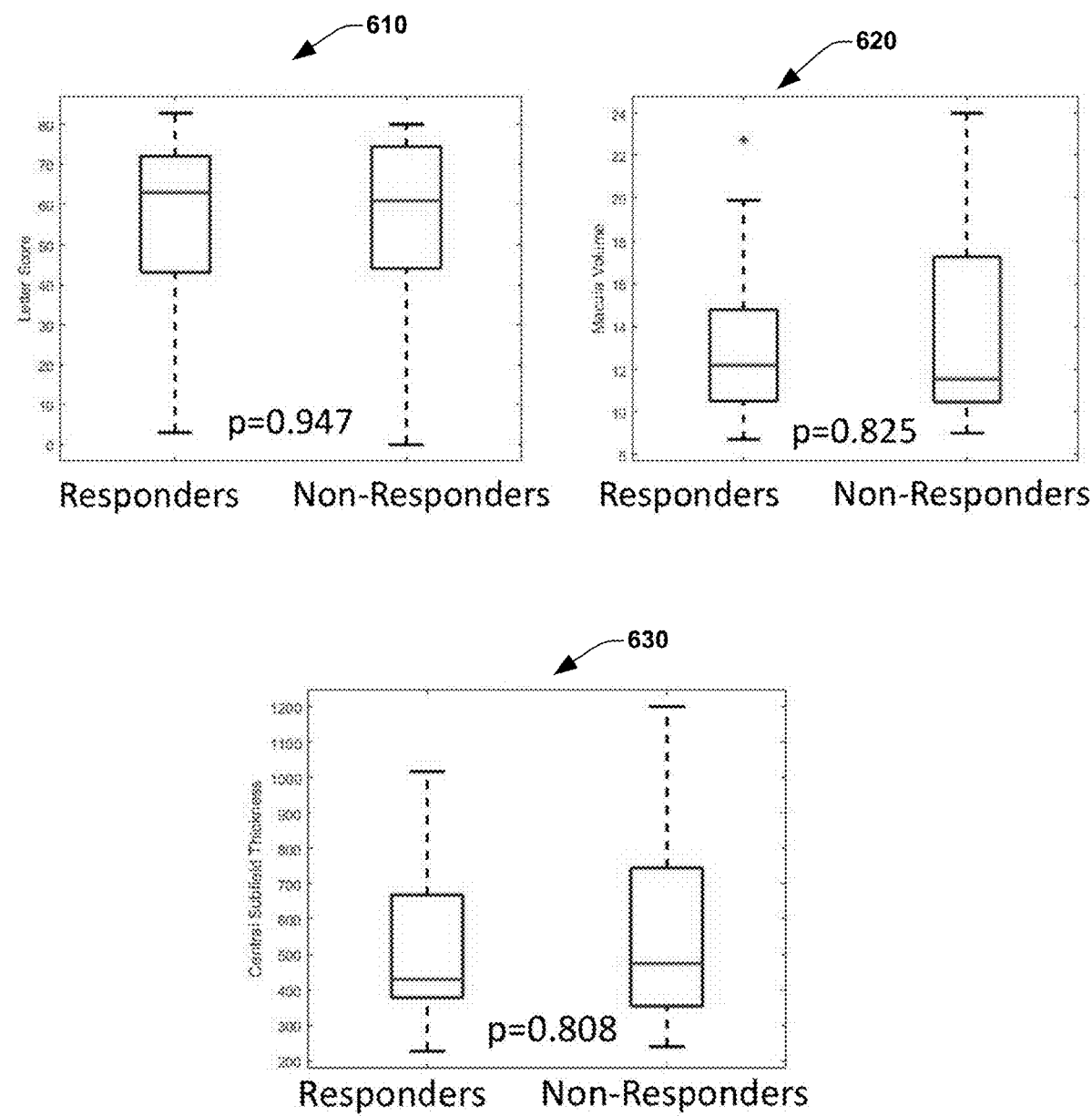
FIG. 6 illustrates box and whisker plots of baseline clinical parameters in distinguishing non-rebounders from rebounders.

Embodiments described herein further facilitate distinguishing eyes based on durability of treatment response with improved accuracy compared to existing approaches that employ clinical parameters. Clinical parameters such as central sub-field thickness (p=0.808), macular volume (p=0.825) and letter scores (p=0.947) on baseline imaging were not found to be statistically significantly different between the two groups. FIG. 6 illustrates Box and whisker plots of the following baseline clinical parameters: Letter Score 610, Macular Volume 620, and Central Subfield Thickness 630.

Embodiments quantify differences in leakage patterns in eyes that require more frequent dosing with eyes that require less frequent dosing. Quantifying this arrangement and spatial proximity characteristics on pre-anti-VEGF therapy UWFA imagery according to various embodiments described herein facilitates discriminating between anti-VEGF therapy candidates who may require less frequent dosing.

While the onset and eventual progression of DME is heavily complex and can derive from a variety of different factors, one aspect that we know plays an important role in both of these processes is leakage, an indicator in BRB breakdown. Ideally, the BRB utilizes different avenues to keep extracellular fluid at an optimal range, i.e. transport mechanisms to pump out fluid and restricted entry to prevent fluid from re-entering. If this sensitive homeostasis is altered, it is an indicator in the breakdown of BRB and consequently, leakage results. Because the eye has no lymphatic system and subsequently lacks a method to remove a large build-up of fluid, leakage is usually followed by edema or swelling on the macula. In this manner, we can see how more disordered leakage patterns can relate to a higher level of disorder within the BRB and thereby, higher progression of the disease as well. If we are able to effectively quantify leakage and its relation to visual acuity, we can use it as a prognostic bio-marker to help clinicians optimally distribute anti-VEGF treatment to patients whose leakage patterns are best suited for this particular type of treatment. Due to the instrumental role that leakage plays in the onset of DME, some existing approaches have previously explored the idea of studying leakage patterns to be able to learn more about the pathophysiology behind the disease. Initially, most of these existing approaches were limited to classifying DME in two distinct categories: diffuse or focal. To distinguish either subcategory from the other, it is essential to first look at an FA image displaying its leakage patterns. Diffuse DME presents in the form of generalized areas of leakage in the area centralis, whereas focal DME is seen as discrete areas of leakage due to the presence of microaneurysms. One existing approach establishes a connection between mean leakage area and mean thickness of the nerve fiber layer (NFL), a retinal structure that is vital in maintaining the permeability of the BRB at homeostatic levels. Some existing approaches employing analysis of leakage from imaging techniques such as SD-OCT have been able use location of leakage to quantify changes in optical reflectivity, a key statistic for clinical follow-ups. Graph constructs may be used to characterize spatial proximity of histopathological primitives such as nuclei. Embodiments quantify those moments of hyper-fluorescence and extract quantitative data that provide a better understanding about how to effectively treat DME. Embodiments quantify characteristics and distribution of leakage patterns taken from FA images that differ across patients who have improved visual acuity after anti-VEGF treatment and employ these differences, or statistical values computed based on such difference, to more accurately predict response to treatment.

Because many first-line therapies center around affecting the blood-retinal barrier, there lies an even greater need to understand the pathophysiology of how leakage is affected by primary treatments options like intravitreal anti-VEGF therapy (i.e., Aflibercept). Visualizing and monitoring any changes in leakage, therefore, offers data of major clinical relevance and can be used to identify potential candidates for therapy with less frequent dosing. Embodiments facilitate identifying potential candidates for therapy with less frequent dosing by not only showing the ability of MST edge length disorder, a quantitative measurements of leakage proximity, to differentiate non-rebounders from rebounders but also by showing its superiority over commonly taken clinical recordings of letter score, macular volume, and central subfield thickness. Embodiments thus provide a measurable improvement over existing methods, systems, apparatus, or other devices or approaches in reliably and accurately predicting patient outcome and improving treatment management in DME.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 100, 200, 300, 1000, 1100, or any other methods or operations described herein. While executable instructions associated with the listed methods or operations are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to distinguishing non-rebounders from rebounders in DME are based on features that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 7:
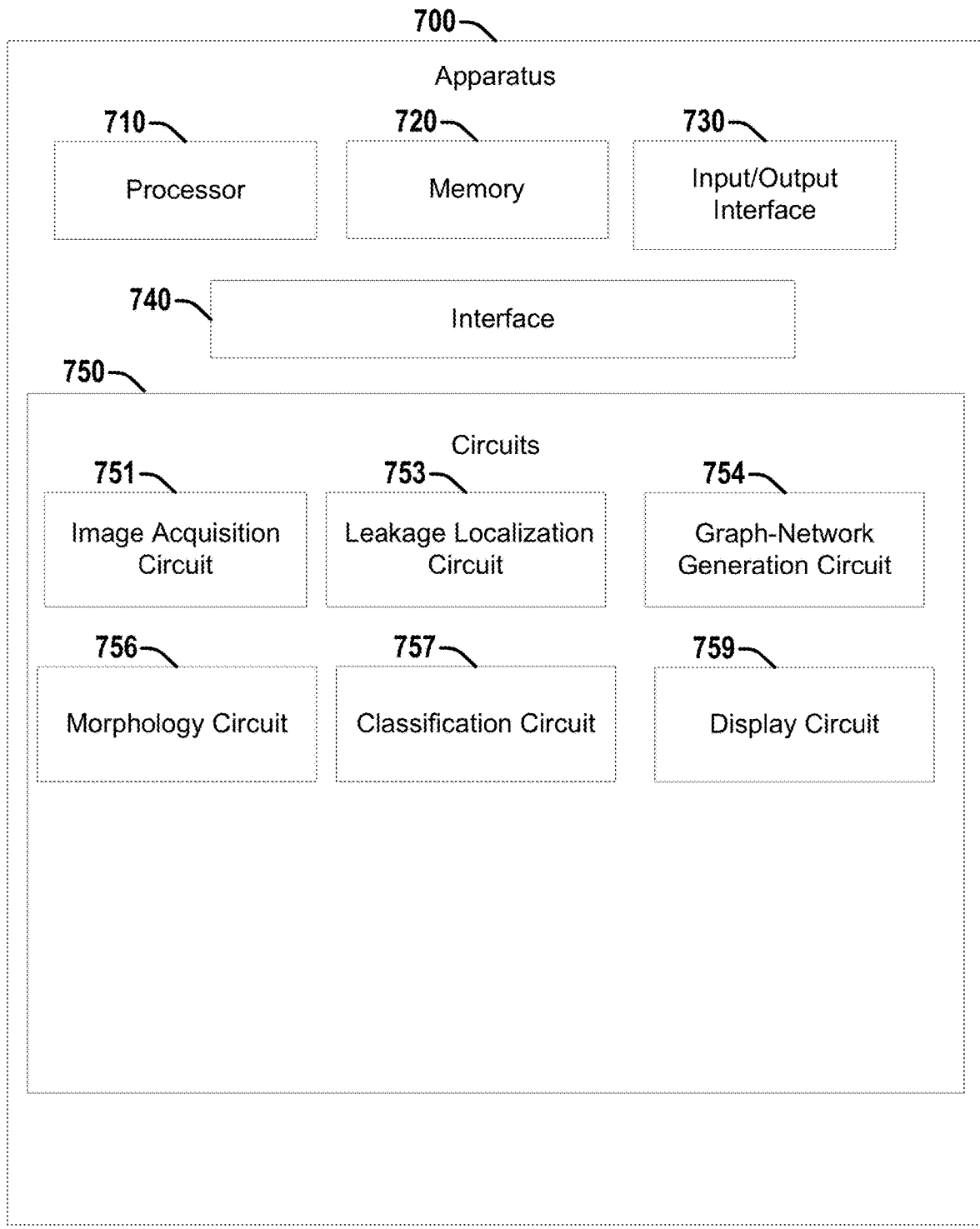
FIG. 7 illustrates a diagram of an example apparatus that can facilitate distinguishing non-rebounders from rebounders according to various embodiments discussed herein.

FIG. 7 illustrates an example apparatus 700 that can facilitate distinguishing non-rebounders from rebounders in DME based on FA imagery (e.g., UWFA imagery), according to various embodiments discussed herein. Apparatus 700 may be configured to perform various techniques, operations, or methods discussed herein, for example, training a machine learning classifier (e.g., QDA classifier, LDA classifier, logistic regression model classifier, CNN classifier, SVM classifier, etc.) based on training data to distinguish non-rebounders from rebounders in DME, or employing such a trained machine learning classifier to generate a classification of a patient based on leakage graphs or leakage morphology features generated from FA imagery. In one embodiment, apparatus 700 includes a processor 710, and a memory 720. Processor 710 may, in various embodiments, include circuitry such as, but not limited to, one or more single-core or multi-core processors. Processor 710 may include any combination of general-purpose processors and dedicated processors (e.g., graphics processors, application processors, etc.). The processor(s) can be coupled with and/or can comprise memory (e.g., memory 720) or storage and can be configured to execute instructions stored in the memory 720 or storage to enable various apparatus, applications, or operating systems to perform operations and/or methods discussed herein.

Memory 720 is configured to store an FA (e.g., UWFA) image associated with a patient, where the image includes a region of interest (ROI) demonstrating DME. The FA image has a plurality of pixels, a pixel having an intensity. In some embodiments, memory 720 can store a training set or testing set of images (e.g., comprising FA images showing retinal vasculatures, along with a known prognosis, or outcome) for training a classifier (e.g., QDA classifier, etc.) to determine a probability that the patient associated with the image is a non-rebounder or rebounder, while in the same or other embodiments, memory 720 can store an FA image of a patient for whom a prediction of tolerance to anti-VEGF therapy, or outcome is to be determined. Memory 720 can be further configured to store one or more clinical features or other data associated with the patient of the FA image.

Apparatus 700 also includes an input/output (I/O) interface 730; a set of circuits 750; and an interface 740 that connects the processor 710, the memory 720, the I/O interface 730, and the set of circuits 750. I/O interface 730 may be configured to transfer data between memory 720, processor 710, circuits 750, and external devices, for example, a medical imaging device such as an FA system or apparatus.

The set of circuits 750 includes an image acquisition circuit 751, a leakage localization circuit 753, a graph-network generation circuit 754, a morphology circuit 756, a DME classification circuit 757, and a display circuit 759.

Image acquisition circuit 751 is configured to access the FA image. Accessing the FA image may include accessing the FA image stored in memory 720. In another embodiment accessing the FA image may include acquiring electronic data, reading from a computer file, receiving a computer file, reading from a computer memory, or other computerized activity not practically performed in the human mind. In one embodiment, the FA image is an ultra-wide field FA (UWFA) image. In one embodiment, the UWFA image may be acquired by an Optos 200Tx scanner.

Leakage localization circuit 753 is configured to generate a leakage localization mask based on the 2D FA image. The leakage localization mask includes a plurality of leakage patches. In one embodiment, leakage localization circuit 753 is configured to generate the leakage localization mask by accessing an early phase FA image and a late phase FA image associated with the patient. In this embodiment, leakage localization circuit 753 is also configured to generate a registered early phase FA image and a registered late phase FA image by registering the early phase FA image with the late phase FA image. In one embodiment, leakage localization circuit 753 is configured to register the early phase FA image with the late phase FA image using Fourier correlation of retinal vascular patterns. In this embodiment, leakage localization circuit 753 is also configured to generate a flattened late phase image based on the registered late phase image. In one embodiment, leakage localization circuit 753 is configured to generate the flattened late phase image by removing an intensity gradient of the optic disc to an image periphery. In this embodiment, leakage localization circuit 753 is also configured to generate a spectrally enhanced late phase image based on the flattened late phase image. In one embodiment, leakage localization circuit 753 is configured to generate the spectrally enhanced late phase image by equalizing the intensity of leakage regions represented in the flattened late phase image. In this embodiment, leakage localization circuit 753 is also configured to remove accentuated vessels from the spectrally enhanced late phase image. In one embodiment, leakage localization circuit 753 is configured to remove accentuated vessels from the spectrally enhanced late phase image by filtering vessels in the registered early phase FA image using a Gaussian convolution kernel, spectrally enhancing the filtered vessels, and subtracting the spectrally enhanced filtered vessels from the registered early phase FA image. In this embodiment, leakage localization circuit 753 is further configured to segment a leakage area based on the spectrally enhanced late phase image using a fixed threshold. In another embodiment, leakage localization circuit 753 is configured to generate the leakage localization mask using other, different techniques.

Graph-network generation circuit 754 is configured to generate a set of leakage graphs based on the leakage localization mask. A node of a member of the set of leakage graphs is a member of the plurality of leakage patches. Graph-network generation circuit 754 is also configured to generate a set of graph-network features based on the set of leakage graphs. In one embodiment, where the set of leakage graphs includes a minimum spanning tree (MST) graph, where a node of the MST graph is a member of the plurality of leakage patches. In this embodiment, the set of graph-network features includes an edge length disorder of MST feature. In another embodiment, graph-network generation circuit 754 may be configured to generate other graph types (e.g., Voronoi, Delaunay), and to generate other graph-network features associated with the other graph-types, respectively.

Morphology circuit 756 is configured to extract a set of morphological features from the FA image based on the leakage localization mask. In one embodiment, the set of morphological features includes at least one of an area feature, a distance to N nearest neighbors feature, or a disorder of variance of distance to N nearest neighbors feature. In another embodiment, morphology circuit 756 may be configured to extract other, different morphological features from the FA image.

DME classification circuit 757 is configured to compute a probability that the patient is a non-rebounder based on the set of graph-network features and the set of morphological features. DME classification circuit 757 is also configured to generate a classification of the patient as a non-rebounder or rebounder based, at least in part, on the probability. In another embodiment, DME classification circuit 757 is also configured to generate a classification of the patient as a responder or non-responder to anti-VEGF therapy based, at least in part, on the probability. In one embodiment, DME classification circuit 757 is configured as a quadratic discriminant analysis (QDA) machine learning classifier. In another embodiment, DME classification circuit 757 is configured as another, different type of machine learning classifier including, for example, an LDA classifier, an SVM classifier, a random forest classifier, or a CNN classifier.

Display circuit 759 is configured to display the classification. Display circuit 759 is also configured to optionally display at least one of the probability, the set of graph-network features, the set of morphological features, a member of set of leakage graphs, or the image. In various embodiments, the classification may include one or more of a most likely outcome (e.g., as determined based on the set of graph-network features, the set of morphological features) such membership in a first class or second, different class (e.g., non-rebounder, rebounder), a probability or confidence associated with a most likely outcome; and/or associated probabilities/confidences associated with each of a plurality of outcomes. Display circuit 759 may be further configured to optionally display the image, the probability, the set of graph-network features, the set of morphological features, or other data associated with the operation of apparatus 700.

Figure 8:
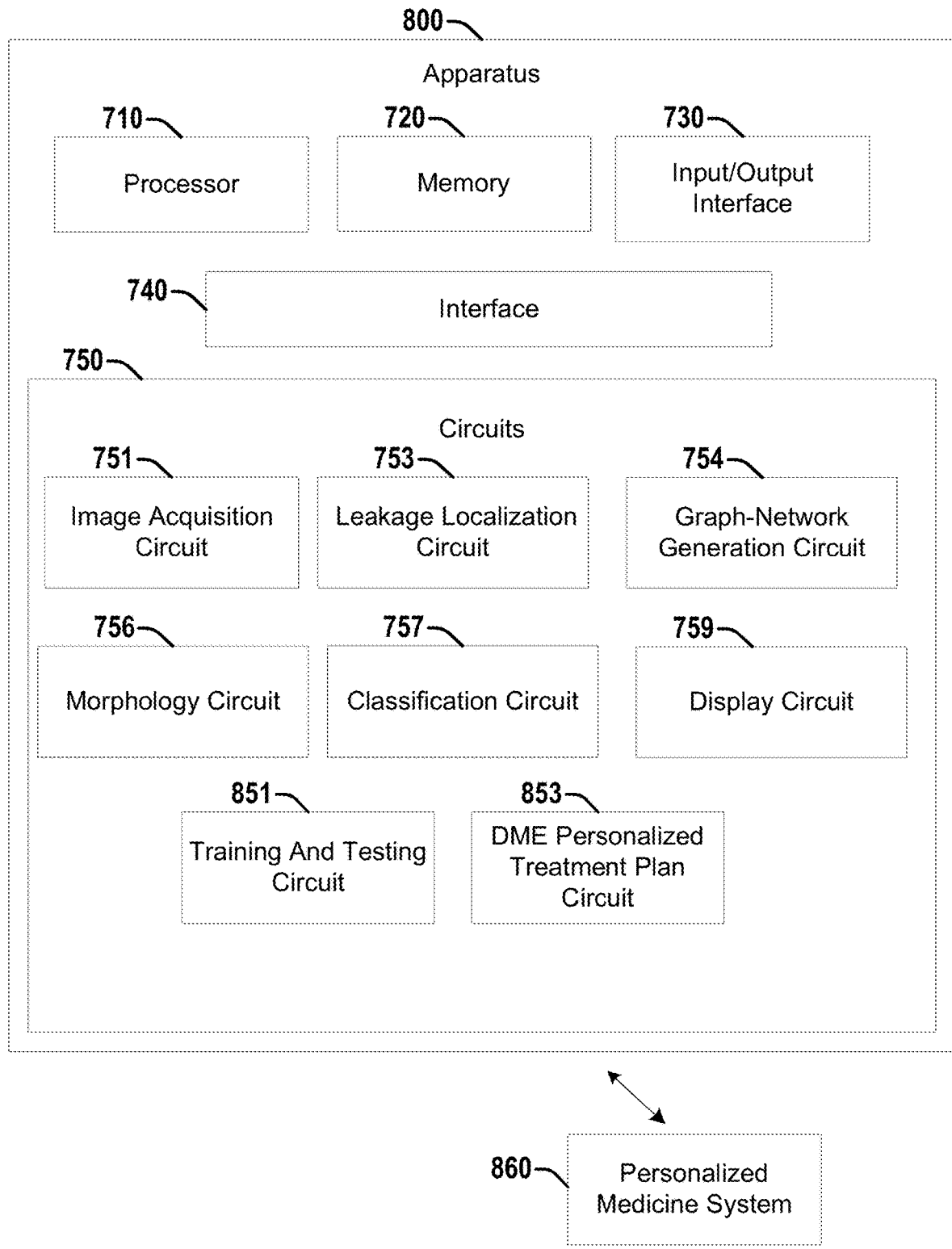
FIG. 8 illustrates a diagram of an example apparatus that can facilitate distinguishing non-rebounders from rebounders according to various embodiments discussed herein.

FIG. 8 illustrates an apparatus 800 that is similar to apparatus 700 but that includes additional elements and details. In one embodiment of apparatus 800, the set of circuits 750 further includes a DME personalized treatment plan circuit 853. DME personalized treatment plan circuit 853 is configured to generate a personalized DME treatment plan based, at least in part, on the classification. DME personalized treatment plan circuit 853 may be configured to generate a personalized treatment plan based, at least in part, on a classification obtained from DME classification circuit 757 or display circuit 759. DME personalized treatment plan circuit 853 may be configured to generate a personalized treatment plan for the patient of whom the image was acquired based, at least in part, on the classification derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, and/or other treatments. Generating a personalized treatment plan based on a more accurate prediction of tolerance to anti-VEGF therapy or a more accurate classification of a patient as a non-rebounder or rebounder facilitates more efficient delivery of costly therapeutic or surgical treatments to patients more likely to benefit from such treatments. For example, the personalized treatment plan may suggest a first surgical treatment, may suggest a first pharmaceutical agent dosage or schedule, and/or other treatments for a patient classified as a non-rebounder, or may suggest a second, different surgical treatment or second, different pharmaceutical agent dosage or schedule or treatments for a patient classified as a rebounder. In this embodiment, display circuit 759 is further configured to optionally display the personalized treatment plan.

In one embodiment of apparatus 800, the set of circuits 750 further includes a training and testing circuit 851. Training and testing circuit 851 is configured to train DME classification circuit 757 on a training cohort according to various embodiments described herein. Training and testing circuit 851 is also configured to optionally test DME classification circuit 757 on a testing cohort, according to various embodiments described herein.

In one embodiment, apparatus 800 further includes personalized medicine device 860. Apparatus 800 may be configured to provide the probability, the classification, a personalized DME treatment plan, or other data to personalized medicine device 860. Personalized medicine device 860 may be, for example, a computer assisted diagnosis (CADx) system or other type of personalized medicine device that can be used to facilitate the prediction of tolerance to anti-VEGF therapy, or to facilitate the classification of a patient as a non-rebounder or rebounder. In one embodiment, DME personalized treatment plan circuit 853 can control personalized medicine device 860 to display the probability, the classification, the set of graph-network features, the set of morphological features, a personalized treatment plan, or other data to on a computer monitor, a smartphone display, a tablet display, or other displays.

Figure 9:
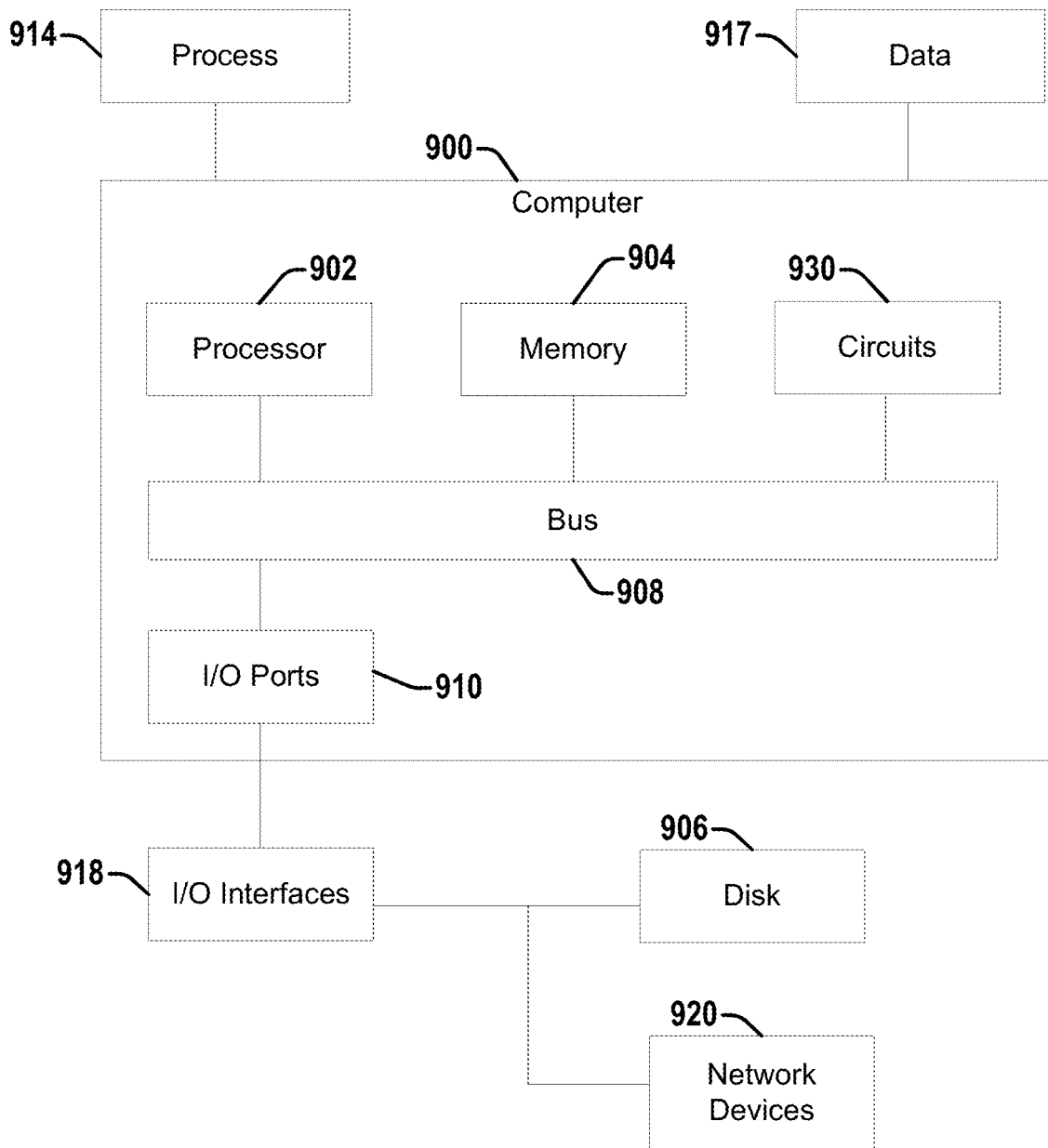
FIG. 9 illustrates a diagram of an example computer in which embodiments described herein may be implemented.

FIG. 9 illustrates an example computer 900 in which example methods illustrated herein can operate and in which example methods, apparatus, circuits, operations, or logics may be implemented. In different examples, computer 900 may be part of an anti-VEGF treatment response prediction system or apparatus, a DME classification system or apparatus, a CADx system, a UWFA system, an MRI system, a CT system, a digital whole slide scanner, or a personalized medicine system, or may be operably connectable to an anti-VEGF treatment response prediction system or apparatus, a DME classification system or apparatus, a CADx system, a UWFA system, an MRI system, a CT system, a digital whole slide scanner, or a personalized medicine system.

Computer 900 includes a processor 902, a memory 904, and input/output (I/O) ports 910 operably connected by a bus 908. In one example, computer 900 may include a set of logics or circuits 930 that perform operations for or a method of predicting tolerance to anti-VEGF therapy, or classifying DME patients as rebounders or non-rebounders on FA imagery, including by using a machine learning classifier. Thus, the set of circuits 930, whether implemented in computer 900 as hardware, firmware, software, and/or a combination thereof may provide means (e.g., hardware, firmware, circuits) for predicting tolerance to anti-VEGF therapy, or classifying DME patients as rebounders or non-rebounders on FA imagery. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized FA images, including UWFA images of tissue demonstrating DME. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 1394, USB, Ethernet).

Computer 900 may interact with input/output devices via I/O interfaces 918 and input/output ports 910. Input/output devices can include, but are not limited to, MRI systems, CT systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

Figure 11:
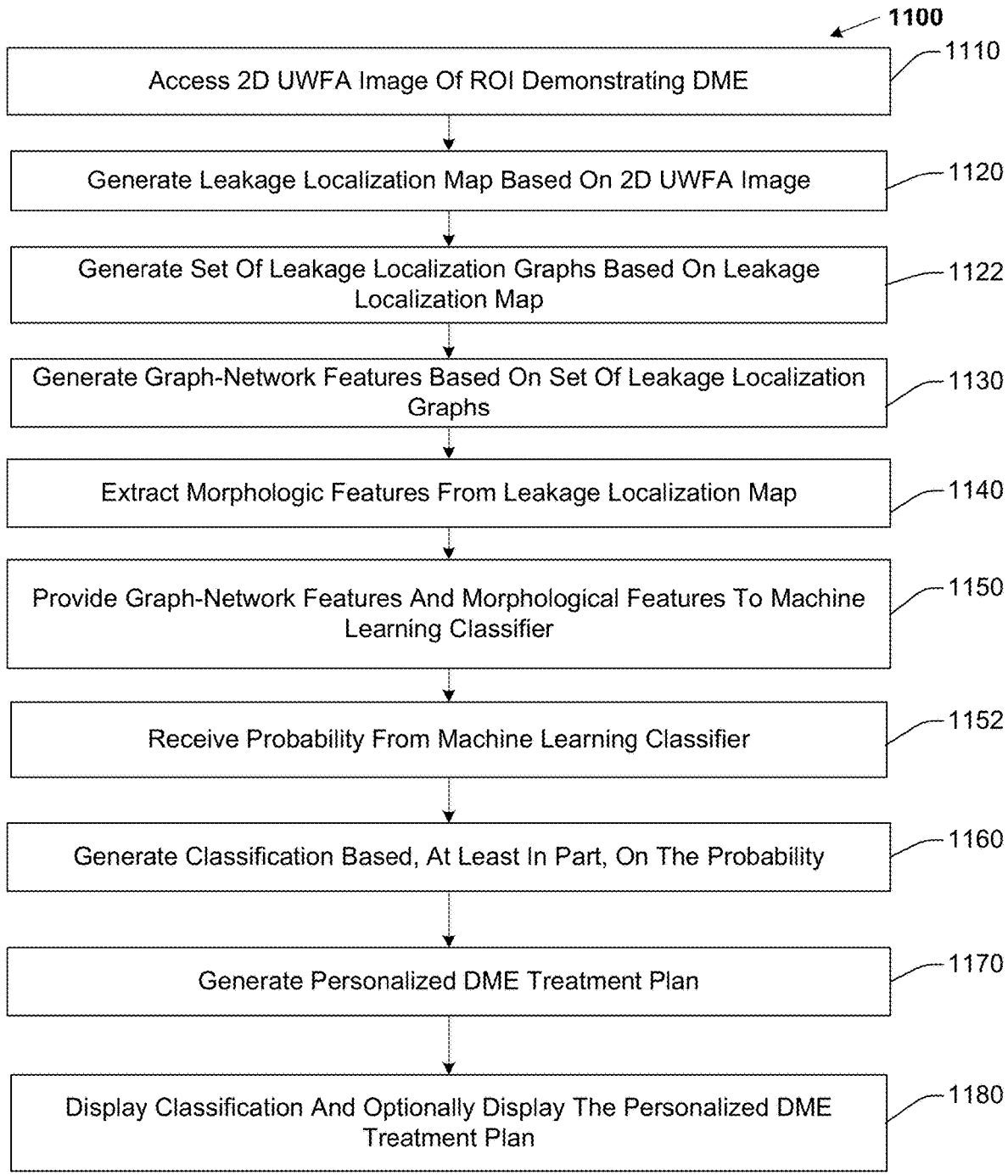
FIG. 11 illustrates a workflow diagram of an example method or set of operations for distinguishing non-rebounders from rebounders according to various embodiments discussed herein.

FIG. 11 illustrates a set of operations or method 1100 for distinguishing non-rebounders from rebounders in DME. Method 1100 includes acquiring electronic data, reading from a computer file, receiving a computer file, reading from a computer memory, or other computerized activity not practically performed in the human mind. Method 1100 includes, at 1110 accessing a pre-anti-vascular endothelial growth factor (anti-VEGF) two-dimensional (2D) ultra-wide field fluorescein angiography (UWFA) mage of a region of interest (ROI) demonstrating diabetic macular edema (DME), where the image is associated with a patient, the image having a plurality of pixels, a pixel having an intensity.

Method 1100 also includes, at 1120, generating a leakage localization mask based on the UWFA image. The leakage localization mask includes a plurality of leakage patches.

Method 1100 also includes, at 1122, generating a set of leakage graphs based on the leakage localization mask. The set of leakage graphs includes a minimum spanning tree (MST) graph, where a node of the MST graph is a member of the plurality of leakage patches.

Method 1100 also includes, at 1130, generating a set of graph-network features based on the set of leakage graphs. The set of graph-network features includes an edge length disorder of MST feature.

Method 1100 also includes, at 1140, extracting a set of morphological features from the UWFA image based on the leakage localization mask. The set of morphological features includes at least one of an area feature, a distance to N nearest neighbors feature, or a disorder of variance of distance to N nearest neighbors feature.

Method 1100 also includes, at 1150, providing the set of graph-network features and the set of morphological features to a quadratic discriminant analysis (QDA) machine learning classifier. The QDA machine learning classifier is configured to distinguish non-rebounders from rebounders in DME based on the set of graph-network features and the set of morphological features.

Method 1100 also includes, at 1152, receiving, from the machine learning classifier, a probability that the patient is a non-rebounder. The machine learning classifier computes the probability based on the set of graph-network features and the set of morphological features.

Method 1100 also includes, at 1160, generating a classification of the patient as a non-rebounder or rebounder. The classification is based, at least in part, on the probability, according to various embodiments described herein.

Method 1100 also includes, at 1170, generating a personalized DME treatment plan. The personalized DME treatment plan is based, at least in part, on the classification.

Method 1100 further includes, at 1180, displaying the classification and optionally displaying at least one of the personalized DME treatment plan, the probability, the set of graph-network features, the set of morphological features, a member of the set of leakage graphs, or the UWFA image.

Examples herein can include subject matter such as an apparatus, an MRI system, a CT system, an optical microscopy system, a personalized medicine system, a CADx system, a processor, a system, circuitry, operations, a method, means for performing operations, acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for distinguishing non-rebounders from rebounders in DME, according to embodiments and examples described.

Example 1 is non-transitory computer-readable storage device storing computer-executable instructions that when executed cause a processor to perform operations, the operations comprising: accessing a two-dimensional (2D) fluorescein angiography (FA) mage of a region of interest (ROI) demonstrating diabetic macular edema (DME), where the image is associated with a patient, where the image has a plurality of pixels, a pixel having an intensity; generating a leakage localization mask based on the FA image, where the leakage localization mask includes a plurality of leakage patches; generating a set of leakage graphs based on the leakage localization mask, where a node of a member of the set of leakage graphs is a member of the plurality of leakage patches; generating a set of graph-network features based on the set of leakage graphs; extracting a set of morphological features from the FA image based on the leakage localization mask; providing the set of graph-network features and the set of morphological features to a machine learning classifier configured to distinguish non-rebounders from rebounders in DME based on the set of graph-network features and the set of morphological features; receiving, from the machine learning classifier, a probability that the patient is a non-rebounder, where the machine learning classifier computes the probability based on the set of graph-network features and the set of morphological features; generating a classification of the patient as a non-rebounder or rebounder based, at least in part, on the probability; and displaying the classification.

Example 2 comprises the subject matter of any variation of any of example(s) 1, where the FA image is a pre-anti-vascular endothelial growth factor (VEGF) treatment ultra-wide field FA (UWFA) image.

Example 3 comprises the subject matter of any variation of any of example(s) 1-2, where generating the leakage localization mask comprises: accessing an early phase FA image and a late phase FA image associated with the patient; generating a registered early phase FA image and a registered late phase FA image by registering the early phase FA image with the late phase FA image; generating a flattened late phase image based on the registered late phase image; generating a spectrally enhanced late phase image based on the flattened late phase image; removing accentuated vessels from the spectrally enhanced late phase image; and segmenting a leakage area based on the spectrally enhanced late phase image using a fixed threshold.

Example 4 comprises the subject matter of any variation of any of example(s) 1-3, where the early phase FA image is registered with the late phase FA image using Fourier correlation of retinal vascular patterns.

Example 5 comprises the subject matter of any variation of any of example(s) 1-4, where generating the flattened late phase image comprises removing an intensity gradient of the optic disc to an image periphery.

Example 6 comprises the subject matter of any variation of any of example(s) 1-5, where generating the spectrally enhanced late phase image comprises equalizing leakage regions represented in the flattened late phase image.

Example 7 comprises the subject matter of any variation of any of example(s) 1-6, where removing accentuated vessels from the spectrally enhanced late phase image comprises: filtering vessels in the registered early phase FA image using a Gaussian convolution kernel; spectrally enhancing the filtered vessels; and subtracting the spectrally enhanced filtered vessels from the registered early phase FA image.

Example 8 comprises the subject matter of any variation of any of example(s) 1-7, where the set of leakage graphs includes a minimum spanning tree (MST) graph, where a node of the MST graph is a member of the plurality of leakage patches.

Example 9 comprises the subject matter of any variation of any of example(s) 1-8, where the set of graph-network features includes an edge length disorder of MST feature.

Example 10 comprises the subject matter of any variation of any of example(s) 1-9, where the set of morphological features includes at least one of an area feature, a distance to N nearest neighbors feature, or a disorder of variance of distance to N nearest neighbors feature.

Example 11 comprises the subject matter of any variation of any of example(s) 1-2, where the machine learning classifier is quadratic discriminant analysis (QDA) classifier.

Example 12 comprises the subject matter of any variation of any of example(s) 1-11, operations further comprising training the machine learning classifier and optionally testing the machine learning classifier.

Example 13 comprises the subject matter of any variation of any of example(s) 1-12, the operations further comprising generating a personalized DME treatment plan based, at least in part, on the classification, and optionally displaying the personalized DME treatment plan.

Example 14 is an apparatus comprising: a processor; a memory configured to store a two-dimensional (2D) fluorescein angiography (FA) image of a region of interest (ROI) demonstrating diabetic macular edema (DME), where the image is associated with a patient, where the image has a plurality of pixels, a pixel having an intensity; an input/output (I/O) interface; a set of circuits; and an interface that connects the processor, the memory, the I/O interface, and the set of circuits, the set of circuits comprising: an image acquisition circuit configured to access a 2D FA image of an ROI demonstrating DME, where the image is associated with a patient, where the image has a plurality of pixels, a pixel having an intensity; a leakage localization circuit configured to: generate a leakage localization mask based on the 2D FA image, where the leakage localization mask includes a plurality of leakage patches; a graph-network generation circuit configured to: generate a set of leakage graphs based on the leakage localization mask, where a node of a member of the set of leakage graphs is a member of the plurality of leakage patches; and generate a set of graph-network features based on the set of leakage graphs; a morphology circuit configured to: extract a set of morphological features from the FA image based on the leakage localization mask; a DME classification circuit configured to: compute a probability that the patient is a non-rebounder based on the set of graph-network features and the set of morphological features; and generate a classification of the patient as a non-rebounder or rebounder based, at least in part, on the probability; and a display circuit configured to displaying the classification and to optionally display at least one of the probability, the set of graph-network features, the set of morphological features, a member of set of leakage graphs, or the image.

Example 15 comprises the subject matter of any variation of any of example(s) 14, where the set of leakage graphs includes a minimum spanning tree (MST) graph, where a node of the MST graph is a member of the plurality of leakage patches, and where the set of graph-network features includes an edge length disorder of MST feature.

Example 16 comprises the subject matter of any variation of any of example(s) 14-15, where the set of morphological features includes at least one of an area feature, a distance to N nearest neighbors feature, or a disorder of variance of distance to N nearest neighbors feature.

Example 17 comprises the subject matter of any variation of any of example(s) 14-16, where the 2D FA image is a pre-anti-vascular endothelial growth factor (VEGF) treatment ultra-wide field FA (UWFA) image.

Example 18 comprises the subject matter of any variation of any of example(s) 14-17, the set of circuits further comprising a training and testing circuit configured to: train the machine learning classifier; and optionally test the machine learning classifier.

Example 19 comprises the subject matter of any variation of any of example(s) 14-18, the set of circuits further comprising a DME personalized treatment plan circuit configured to: generate a personalized DME treatment plan based, at least in part, on the classification; and optionally control the display circuit to display the personalized DME treatment plan.

Example 20 is non-transitory computer-readable storage device storing computer-executable instructions that when executed by a computer control the computer to perform a method, the method comprising: accessing a pre-anti-vascular endothelial growth factor (anti-VEGF) two-dimensional (2D) ultra-wide field fluorescein angiography (UWFA) mage of a region of interest (ROI) demonstrating diabetic macular edema (DME), where the image is associated with a patient, the image having a plurality of pixels, a pixel having an intensity; generating a leakage localization mask based on the UWFA image, where the leakage localization mask includes a plurality of leakage patches; generating a set of leakage graphs based on the leakage localization mask, where the set of leakage graphs includes a minimum spanning tree (MST) graph, where a node of the MST graph is a member of the plurality of leakage patches; generating a set of graph-network features based on the set of leakage graphs, where the set of graph-network features includes an edge length disorder of MST feature; extracting a set of morphological features from the UWFA image based on the leakage localization mask, where the set of morphological features includes at least one of an area feature, a distance to N nearest neighbors feature, or a disorder of variance of distance to N nearest neighbors feature; providing the set of graph-network features and the set of morphological features to a quadratic discriminant analysis (QDA) machine learning classifier configured to distinguish non-rebounders from rebounders in DME based on the set of graph-network features and the set of morphological features; receiving, from the machine learning classifier, a probability that the patient is a non-rebounder, where the machine learning classifier computes the probability based on the set of graph-network features and the set of morphological features; generating a classification of the patient as a non-rebounder or rebounder based, at least in part, on the probability; generating a personalized DME treatment plan based, at least in part, on the classification; and displaying the classification and optionally displaying at least one of the probability, the set of graph-network features, the set of morphological features, a member of the set of leakage graphs, or the UWFA image.

Example 21 comprises a machine readable storage device that stores instructions for execution by a processor to perform any of the described operations of examples 1-20.

Example 22 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed cause a processor to perform operations, the operations comprising:
   accessing a two-dimensional (2D) fluorescein angiography (FA) image of a region of interest (ROI) demonstrating diabetic macular edema (DME), where the image is associated with a patient, where the image has a plurality of pixels, a pixel having an intensity;
   generating a leakage localization mask based on the FA image, where the leakage localization mask includes a plurality of leakage patches;
   generating a set of leakage graphs based on the leakage localization mask, where a node of a member of the set of leakage graphs is a member of the plurality of leakage patches;
   generating a set of graph-network features based on the set of leakage graphs;
   extracting a set of morphological features from the FA image based on the leakage localization mask;
   providing the set of graph-network features and the set of morphological features to a machine learning classifier configured to distinguish non-rebounders from rebounders in DME based on the set of graph-network features and the set of morphological features;
   receiving, from the machine learning classifier, a probability that the patient is a non-rebounder, where the machine learning classifier computes the probability based on the set of graph-network features and the set of morphological features;
   generating a classification of the patient as a non-rebounder or rebounder based, at least in part, on the probability; and
   displaying the classification.

2. The non-transitory computer-readable storage device of claim 1, where the FA image is a pre-anti-vascular endothelial growth factor (VEGF) treatment ultra-wide field FA (UWFA) image.

3. The non-transitory computer-readable storage device of claim 1, where generating the leakage localization mask comprises:
   accessing an early phase FA image and a late phase FA image associated with the patient;
   generating a registered early phase FA image and a registered late phase FA image by registering the early phase FA image with the late phase FA image;
   generating a flattened late phase image based on the registered late phase image;
   generating a spectrally enhanced late phase image based on the flattened late phase image;
   removing accentuated vessels from the spectrally enhanced late phase image; and
   segmenting a leakage area based on the spectrally enhanced late phase image using a fixed threshold.

4. The non-transitory computer-readable storage device of claim 3, where the early phase FA image is registered with the late phase FA image using Fourier correlation of retinal vascular patterns.

5. The non-transitory computer-readable storage device of claim 4, where the set of graph-network features includes an edge length disorder of MST feature.

6. The non-transitory computer-readable storage device of claim 3, where generating the flattened late phase image comprises removing an intensity gradient of the optic disc to an image periphery.

7. The non-transitory computer-readable storage device of claim 6, where generating the spectrally enhanced late phase image comprises equalizing leakage regions represented in the flattened late phase.

8. The non-transitory computer-readable storage device of claim 3, where removing accentuated vessels from the spectrally enhanced late phase image comprises:
  filtering vessels in the registered early phase FA image using a Gaussian convolution kernel;
  spectrally enhancing the filtered vessels; and
  subtracting the spectrally enhanced filtered vessels from the registered early phase FA image.

9. The non-transitory computer-readable storage device of claim 1, where the set of leakage graphs includes a minimum spanning tree (MST) graph, where a node of the MST graph is a member of the plurality of leakage patches.

10. The non-transitory computer-readable storage device of claim 1, where the set of morphological features includes at least one of an area feature, a distance to N nearest neighbors feature, or a disorder of variance of distance to N nearest neighbors feature.

11. The non-transitory computer-readable storage device of claim 1, where the machine learning classifier is quadratic discriminant analysis (QDA) classifier.

12. The non-transitory computer-readable storage device of claim 11, the operations further comprising training the machine learning classifier and optionally testing the machine learning classifier.

13. The non-transitory computer-readable storage device of claim 1, the operations further comprising generating a personalized DME treatment plan based, at least in part, on the classification, and optionally displaying the personalized DME treatment plan.

14. An apparatus comprising:
  a processor;
  a memory configured to store a two-dimensional (2D) fluorescein angiography (FA) image of a region of interest (ROI) demonstrating diabetic macular edema (DME), where the image is associated with a patient, where the image has a plurality of pixels, a pixel having an intensity;
  an input/output (I/O) interface;
  a set of circuits; and
  an interface that connects the processor, the memory, the I/O interface, and the set of circuits, the set of circuits comprising:
  an image acquisition circuit configured to access a 2D FA image of an ROI demonstrating DME, where the image is associated with a patient, where the image has a plurality of pixels, a pixel having an intensity;
  a leakage localization circuit configured to:
    generate a leakage localization mask based on the 2D FA image, where the leakage localization mask includes a plurality of leakage patches;
  a graph-network generation circuit configured to:
    generate a set of leakage graphs based on the leakage localization mask, where a node of a member of the set of leakage graphs is a member of the plurality of leakage patches; and
    generate a set of graph-network features based on the set of leakage graphs;
  a morphology circuit configured to:
    extract a set of morphological features from the FA image based on the leakage localization mask;
  a DME classification circuit configured to:
    compute a probability that the patient is a non-rebounder based on the set of graph-network features and the set of morphological features; and
    generate a classification of the patient as a non-rebounder or rebounder based, at least in part, on the probability; and
  a display circuit configured to displaying the classification and to optionally display at least one of the probability, the set of graph-network features, the set of morphological features, a member of set of leakage graphs, or the image.

15. The apparatus of claim 14, where the set of leakage graphs includes a minimum spanning tree (MST) graph, where a node of the MST graph is a member of the plurality of leakage patches, and where the set of graph-network features includes an edge length disorder of MST feature.

16. The apparatus of claim 14, where the set of morphological features includes at least one of an area feature, a distance to N nearest neighbors feature, or a disorder of variance of distance to N nearest neighbors feature.

17. The apparatus of claim 14, where the 2D FA image is a pre-anti-vascular endothelial growth factor (VEGF) treatment ultra-wide field FA (UWFA) image.

18. The apparatus of claim 14, the set of circuits further comprising a training and testing circuit configured to:
  train the machine learning classifier; and
  optionally test the machine learning classifier.

19. The apparatus of claim 14, the set of circuits further comprising a DME personalized treatment plan circuit configured to:
  generate a personalized DME treatment plan based, at least in part, on the classification; and
  optionally control the display circuit to display the personalized DME treatment plan.

20. A non-transitory computer-readable storage device storing computer-executable instructions that when executed by a computer control the computer to perform a method, the method comprising:
  accessing a pre-anti-vascular endothelial growth factor (anti-VEGF) two-dimensional (2D) ultra-wide field fluorescein angiography (UWFA) image of a region of interest (ROI) demonstrating diabetic macular edema (DME), where the image is associated with a patient, the image having a plurality of pixels, a pixel having an intensity;
  generating a leakage localization mask based on the UWFA image, where the leakage localization mask includes a plurality of leakage patches;
  generating a set of leakage graphs based on the leakage localization mask, where the set of leakage graphs includes a minimum spanning tree (MST) graph, where a node of the MST graph is a member of the plurality of leakage patches;
  generating a set of graph-network features based on the set of leakage graphs, where the set of graph-network features includes an edge length disorder of MST feature;

extracting a set of morphological features from the UWFA image based on the leakage localization mask, where the set of morphological features includes at least one of an area feature, a distance to N nearest neighbors feature, or a disorder of variance of distance to N nearest neighbors feature;

providing the set of graph-network features and the set of morphological features to a quadratic discriminant analysis (QDA) machine learning classifier configured to distinguish non-rebounders from rebounders in DME based on the set of graph-network features and the set of morphological features;

receiving, from the machine learning classifier, a probability that the patient is a non-rebounder, where the machine learning classifier computes the probability based on the set of graph-network features and the set of morphological features;

generating a classification of the patient as a non-rebounder or rebounder based, at least in part, on the probability;

generating a personalized DME treatment plan based, at least in part, on the classification; and displaying the classification and optionally displaying at least one of the probability, the set of graph-network features, the set of morphological features, a member of the set of leakage graphs, or the UWFA image.

* * * * *

UNITED STATES PATENT AND TRADEMARK OFFICE
CERTIFICATE OF CORRECTION

PATENT NO. : 10,943,348 B2
APPLICATION NO. : 16/415833
DATED : March 9, 2021
INVENTOR(S) : Anant Madabhushi et al.

It is certified that error appears in the above-identified patent and that said Letters Patent is hereby corrected as shown below:

In the Specification

Column 1, Lines 20 through 26; please replace "This invention was made with government support under the grant(s) CA199374, CA202752, CA208236, CA216579, CA220581, CA239055 and RR012463 awarded by the National Institutes of Health. Also grants W81XWH-18-1-0440, W81XWH-15-1-0558, and W81XWH-16-1-0329 awarded by the Department of Defense. The government has certain rights in the invention." with --This invention was made with government support under the grants CA199374, CA202752, CA208236, CA216579, CA220581, CA239055 and RR012463 awarded by the National Institutes of Health. Also grants W81XWH-18-1-0440, W81XWH-15-1-0558, and W81XWH-16-1-0329 awarded by the Department of Defense. The government has certain rights in the invention.--

Signed and Sealed this
Fourteenth Day of September, 2021

Drew Hirshfeld
*Performing the Functions and Duties of the
Under Secretary of Commerce for Intellectual Property and
Director of the United States Patent and Trademark Office*